United States Patent [19]

Holmes

[11] Patent Number: 4,971,905

[45] Date of Patent: Nov. 20, 1990

[54] DIAGNOSIS OF CANCEROUS OR PRECANCEROUS CONDITIONS IN HUMAN SECRETORY EPITHELIA BY ENZYME ACTIVITY OF β-1-3N-ACETYLGLUCOSAMINYLTRANSFERASE

[75] Inventor: Eric H. Holmes, Bothell, Wash.

[73] Assignee: Pacific Northwest Research Foundation, Seattle, Wash.

[21] Appl. No.: 84,302

[22] Filed: Aug. 11, 1987

[51] Int. Cl.$^5$ ............................................. C12Q 1/48
[52] U.S. Cl. ...................................... 435/15; 435/810
[58] Field of Search .................................. 435/15, 810

[56] References Cited

U.S. PATENT DOCUMENTS 4,471,057 9/1984 Koprowski et al. .
4,757,003 7/1988 Matsumoto et al. ................ 436/813

FOREIGN PATENT DOCUMENTS 0272603 6/1988 European Pat. Off. .
89/02474 3/1989 World Int. Prop. O. .

OTHER PUBLICATIONS

Lamont et al., *Jour. Natl. Cancer Inst.*, 54, 53–56, 1975.
Holmes et al., *Jour. Biol. Chem.*, 262, 15649–15658, 1987.
Hakamori et al., *Jour. Natl. Cancer Inst.*, 71, 231–251, 1983.

*Primary Examiner*—Esther L. Kepplinger
*Assistant Examiner*—David A. Saunders
*Attorney, Agent, or Firm*—David L. Garrison

[57] ABSTRACT

A method for diagnostic or prognostic monitoring of premalignant or malignant conditions of human secretory epithelia, particularly colonic epithelia, by determining the extent of expression of a β1-3N-acetylglucosaminyltransferase is described. Associated with the expression of a wide variety of carbohydrate antigens in adenocarcinomas is the induction of β1-3N-acetylglucosaminyltransferase in epithelial cells. This enzyme is not found in normal, healthy adult colonic epithelial cells and thus indicates a novel and potentially sensitive method for screening the disease status of individuals.

4 Claims, 14 Drawing Sheets 1  2  3  4

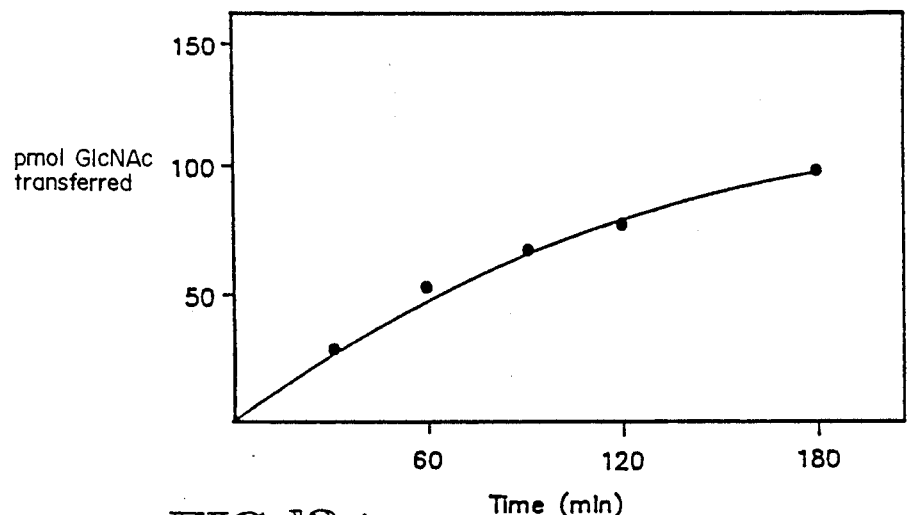
FIG. 13A
FIG. 13B
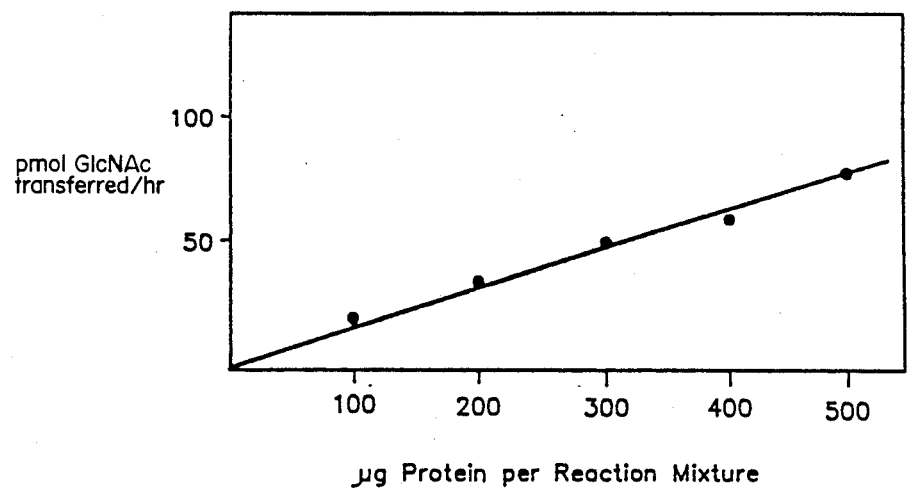

DIAGNOSIS OF CANCEROUS OR PRECANCEROUS CONDITIONS IN HUMAN SECRETORY EPITHELIA BY ENZYME ACTIVITY OF β-1-3N-ACETYLGLUCOSAMINYLTRANSFERASE

FIELD OF THE INVENTION

This invention relates to the detection of premalignant and malignant conditions of human tissues by analyzing and monitoring a specific enzymatic lesion responsible for characteristic changes in carbohydrate antigens expressed at the cell surface and released into serum.

BACKGROUND OF THE INVENTION

A variety of cases of both spontaneously occurring human cancers and experimental cancers in animals have been characterized as possessing tumor associated carbohydrate markers. Carbohydrate antigens carrying the Le$^x$ determinant (Galβ1-4[Fucα1-3]GlcNAc-) have been found to accumulate in large quantity in human adenocarcinomas. A collection of carbohydrate structures have been determined that have in common the presence of one or more α1-3 linked fucose residues on GlcNAc, the hallmark of the Le$^x$ determinant structure. Further derivatives of the Le$^x$ structure have been demonstrated. The presence of α1-3 linked fucose residues on both α2-3 and α2-6 terminally sialylated oligosaccharides have given rise to the sialyl-Le$^x$ determinant structure. In addition, α1-3 fucosylation of blood group H structures have given rise to the Ley and trifucosyl Le$^y$ determinants.

With the advent of monoclonal antibody technology, a variety of highly specific antibodies have been generated which are directed to many of these related carbohydrate structures. Monoclonal antibodies specific for Le$^x$ and sialyl Le$^x$ determinant carrying structures have been used for immunostaining tissue sections from normal human fetal and adult tissues as well as human adenocarcinomas. The antibody FH4 (specific for di- or trimeric Le$^x$ determinant) strongly stained a variety of human adenocarcinomas and fetal gastrointestinal and pulmobronchial epithelia during organogenesis. In adult tissues very little staining was observed. Only a small number of normal cells, such as parietal cells of gastric epithelia and Paneth's cells of intestinal mucosa, were positively stained.

Localization and distribution of the sialyl Le$^x$ antigen has been studied using the sialyl Le$^x$ determinant specific antibody FH6. These results indicated that a large variety of embryonic and fetal tissues showed positive staining particularly in the epithelial cell layer, however, no staining was observed in various normal adult tissues. Positive staining was also observed in a variety of cancer tissues tested. More recently, the expression of the Ley antigen has been studied in premalignant and malignant lesions of human colonic epithelium. These results indicated that Le$^y$ was expressed in colorectal adenocarcinomas and in colonic polyps which showed a greater degree of dysplasia. These results indicate that expression of a variety of glycolipids containing internal α1-3 linked fucose residues on GlcNAc is associated with fetal development and oncogenesis in these tissues and such expression is oncofetal. Another related class of carbohydrate antigens that have been described as tumor-associated contain α1-4 linked fucose residues on GlcNAc. These are isomeric structures of the Le$^x$ structures in that they differ in the linkage position of the galactose and fucose residues. These structures (Le$^a$) are part of the Lewis blood group system and are expressed in human cancers in association with the Lewis antigen status of the individual. The most highly studied antigen in this group is an α2-3 sialylated form of the Le$^a$ antigen. An antibody, CA 19-9, specific for this structure has an apparent specificity for gastrointestinal and pancreatic cancer.

These related antigens expressing α1-3 or α1-4-fucose residues are derivatives of a commonly found core carbohydrate structure called the lactoseries. Structures containing β1-3 linked terminal Gal residues and α1-4 linked fucose residues represent type 1 chain structures while terminal β1-4 Gal residues which can carry α1-3 linked fucose residues are type 2 chain structures. Study of these antigens have indicated that the expression of both type 1 and type 2 chain based antigens are considered to be oncofetal in human colonic tissues since they are expressed at certain stages of normal development, decrease greatly in adult tissues, and re-appear in association with oncogenesis.

The great diversity of structures that occur in association with oncogenesis based on lacto-series chains along with the serologic diversity of individuals have so far prevented the finding of a single antibody which could recognize with great fidelity a premalignant or malignant condition necessary for diagnostic screening. This has limited the potential of the use of these carbohydrate structures in defining the disease status. The presence of a complex diversity of related structures in premalignant and malignant tissues tend to obscure the specific biochemical event responsible for their synthesis. Identification and exploitation of the specific lesion responsible for expression of both type 1 and 2 lacto-series chain structures could give rise to a general and sensitive process for survey of the disease status of any individual irrespective of their serological status. This would represent obvious improvements in the use of carbohydrate structures as sentinels for early stages in oncogenesis. Described in this application are results which indicate an alteration common to all colonic adenocarcinomas which is responsible for the formation of this complex series of carbohydrateantigens. This forms the basis of an obvious method for diagnostic or prognostic screening of individuals which would represent a significant improvement over current technology.

SUMMARY OF THE INVENTION

This invention provides a method and process for identification of synthesis of carbohydrate antigens associated with many human tumors which would have important diagnostic applications. Formation of all type 1 and 2 lacto-series chain based antigens found to be tumor-associated in human ad-enocarc-inomas result as a consequence of activation of a normally unexpressed β1-3N-acetylglucosaminyltransferase. This enzyme, in combination with a variety of normally expressed glycosyltransferases, give rise to abundant quantities (in terms of both diverse structures and chemical amounts) of tumor associated antigens that are expressed at premalignant and malignant stages of oncogenesis. A sensitive survey of the disease status may be achieved by determining the extent of the expression of this activity through a variety of potential leans. These could include activity present in serum or biopsy tissues, the amount of β1–3 linked GlcNAc residues in serum or tissue based carbohydrate structures, or other means to assess the expression of this activity.

BRIEF DESCRIPTION OF THE DRAWINGS

FIG. 13 shows that conditions for assay of β1–3N-acetylgluoosaminyltransferase activity have been defined which yield results that are linear with respect to both time and protein concentration.

DESCRIPTION OF THE PREFERRED EMBODIMENT

Figure 1:
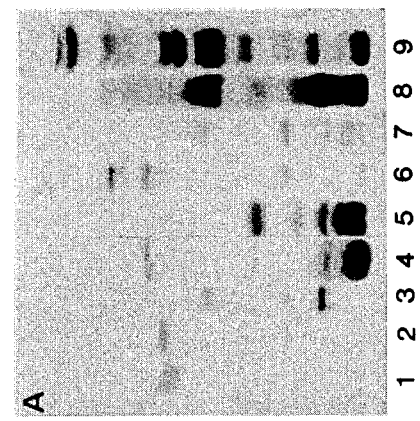
FIG. 1 shows thin layer chromatography profiles of neutral glycolipids from normal tissues and tumors and demonstrates the absence in normal adult colonic mucosa of significant quantities of Le$^x$ structures (Panel B) or underivatized type 2 chain precursor structures (Panel C). These structures are found in abundant quantity in neutral glycolipids from colonic adenocarcinoma tumors.
Figure 1:
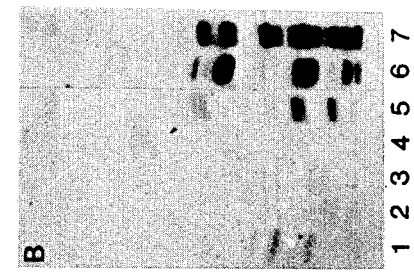
Figure 1:
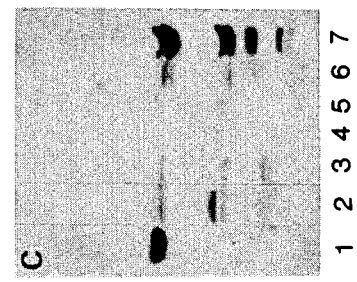
Figure 1:
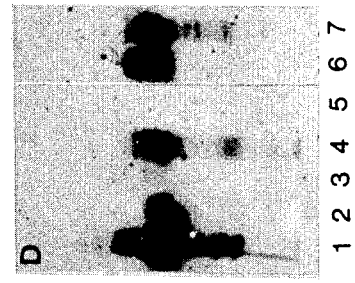

Pursuant to this invention the cellular expression of diagnostic type 1 and 2 lacto-series tumor-associated carbohydrate structures is detected by means to measure β1–3N-acetylglucosaminyltransferase action or activity. No single in vivo derived type 1 or type 2 lacto-series structure has complete specificity for premalignant or malignant status in human adenocarcinomas, although a wide variety of related structures are formed. The status of β1–3N-acetylglucosaminyltransferase activity or action which is activated in order to express all of these antigens in adenocarcinomas and is therefore the single enzymatic lesion responsible for the expression of type 1 and 2 chain based antigens is the most specific and universal sentinel for disease progression. This would have diagnostic and prognostic applications which would yield a significant improvement over current technology.

As described in the following series of Examples, the carbohydrate structures found on both normal human colonic mucosa and derived colonic adenocarcinoma tumors and cell lines were characterized by extracting the cellular glycolipids with isopropanol:hexane:water (55:25:20), separation into neutral glycolipid and ganglioside fractions by chromatography on a DEAE-Sephadex column, and analysis by thin layer chromatography and thin layer chromatography immunostain procedures. These procedures showed that tumor cells and tissues contained a wide variety of lacto-series antigens which displayed diverse discrete antigenic determinants. These carbohydrate structures were almost undetectable in extracts from normal mucosal epithelial cells.

Further characterization of the differential biosynthesis of lacto-series carbohydrate structures in normal colonic mucosa and colonic adenocarcinoma cells and tumors by analysis of the biosynthetic enzymes involved in the synthesis of these carbohydrate structures yielded a novel finding. Despite the absence of fucosylated derivatives of lacto-series glycolipids in normal mucosal epithelia, a very high activity of a fucosyltransferase was found. However, normal adult colonic epithelial cells were shown by immunofluorescence staining on frozen tissue sections to lack type 2 lacto-series chain expression. Thus the absence of fucosylated derivatives of type 2 chains is due to the control of type 2 chain expression. The expression of these carbohydrate antigens has been considered to be oncofetal in nature in that they are expressed during normal development, are lost in adult tissues, and re-appear during oncogenesis in human colon. As a control, immunofluorescence staining of fetal colon indicated the abundant presence of type 2 chain precursors and the resultant fucosylated derivatives. This identified the key to the expression of the entire diverse class of tumor-associated antigens as control of expression of lacto-series core carbohydrate chains. Further characterization of the biosynthesis of lacto-series core chains by direct enzymatic analysis and analysis of in situ biosynthesis of lacto-series core chains in normal colonic epithelial cells by an immunohistological technique indicated that the key enzyme that is missing, or only very minimally expressed, in normal adult colonic epithelial cells is a β1–3-N-acetylglucosaminyltransferase responsible for the first committed step in lacto-series core chain synthesis.

As a consequence of this finding, it is immediately obvious that a more universal and potentially more sensitive diagnostic marker for premalignant and malignant conditions is the status of this $\beta$1-3-N-acetylglucosaminyltransferase in adult colonic tissues. Thus, screening of individuals for the status of this activity, the expression of this enzyme protein, or the direct or indirect analysis of the action of this enzyme by incorporation of $\beta$1-3 linked GlcNAc residues into lacto-series carbohydrate chains represents a new and useful basis for disease diagnosis. With this information as a basis, the disclosure contained herein describes potential diagnostic applications of this marker. The following Examples are presented to illustrate the advantages of the present invention and to assist one of ordinary skill in making and using the same. The following Examples are not intended in any way to otherwise limit the score of the disclosure or the protection granted by Letters Patent hereon.

Various aspects of the examples set out below are graphically desplayed in the attached figures and photographs. To more clearly describe the invention, these figures and photographs are described briefly in the following Figure Legends.

FIGURE LEGENDS

FIG. 1. Thin layer chromatographic and immunostain analysis of neutral glycolipids isolated from normal human colonic mucosa and colonic adenocarcinomas. Panel A, neutral glycolipids of the indicated fractions visualized by orcinol spray. Lane 1, standard $Lc_4$; lane 2, standard $nLc_4$; lane 3, standard $III^3V^3Fuc_2nLc_6$ and $III^3FucnLc_4$ (in terms of increasing mobility); lane 4, type "O" whole blood cell Folch upper neutral fraction; lane 5 normal human liver upper neutral fraction; lane 6, normal human colonic mucosa total neutral glycolipids; lane 7, NCI-H69 cell neutral glycolipids; lane 8, human colonic adenocarcinoma FT-620 neutral glycolipids; lane 9, human colonic adenocarcinoma TG-115 neutral glycolipids. Panel B, immunostain analysis of glycolipid fractions with the Le$^x$ specific antibody WHGS-29-1. Lane 1, standard $III^3V^3Fuc_2nLc_6$, $V^3FucnLc_6$, and $III^3FucnLc_4$ (in terms of increasing mobility); lane 2, type "O" whole blood cell upper neutral glycolipids; lane 3, normal human liver upper neutral glycolipids; lane 4, normal human colonic mucosa neutral glycolipids; lane 5, NCI-H69 cell neutral glycolipids; lane 6, neutral glycolipids from human colonic adenocarcinoma FT-620; lane 7, neutral glycolipids from human colonic adenocarcinoma TG-115. Panel C, immunostain analysis of glycolipid fractions with antibody 1B2 specific for type 2 chain core structures. Lane 1, standard $nLc_4$; lane 2 type "O" whole blood cell upper neutral glycolipids; lane 3, normal human liver upper neutral glycolipids; lane 4, neutral glycolipids from normal human colonic mucosa; lane 5, neutral glycolipids from NCI-H69 cells; lane 6, neutral glycolipids from human colonic adenocarcinoma FT-620; lane 7, neutral glycolipids from human colonic adenocarcinoma TG-115. Panel D, immunostain analysis of glycolipid fractions with anti-Le$^a$ antibody. Lane 1, neutralglycolipids from human meconium; lane 2, type "O" whole blood cell upper neutral glycolipids; lane 3, normal human liver upper neutral glycolipids; lane 4, neutral glycolipids from normal human colonic mucosa; lane 5, neutral glycolipids from NCI-H69 cells; lane 6, neutral glycolipids from human colonic adenocarcinoma FT-620; lane 7, neutral glycolipids from human colonic adenocarcinoma TG-115. The plates were developed in a solvent system composed of $CHCl_3:CH_{OH:H_2O}$, 56:38:10. Conditions of immuno stain analysis were as described under "Experimental Procedures".

Figure 2:
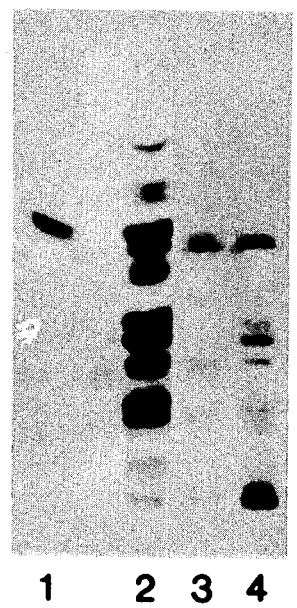
FIG. 2 shows that gangliosides isolated from normal adult colonic mucosa contain most of the type 2 chain core structures present in normal mucosa.

FIG. 2. Immunostain analysis of desialylated gangliosides of normal human colonic mucosa and NCI-H69 cells with the type 2 chain specific antibody 1B2. Lane 1, standard $nLc_4$; lane 2, desialylated gangliosides from type "O" whole blood cells; lane 3, desialylated gangliosides from NCI-H69 cells; lane 4, desialylated gangliosides from normal human colonic mucosa. The plate was developed in a solvent composed of $CHCl_3:CH_3OH:H_2O$, 56:38:10.

Figure 3:
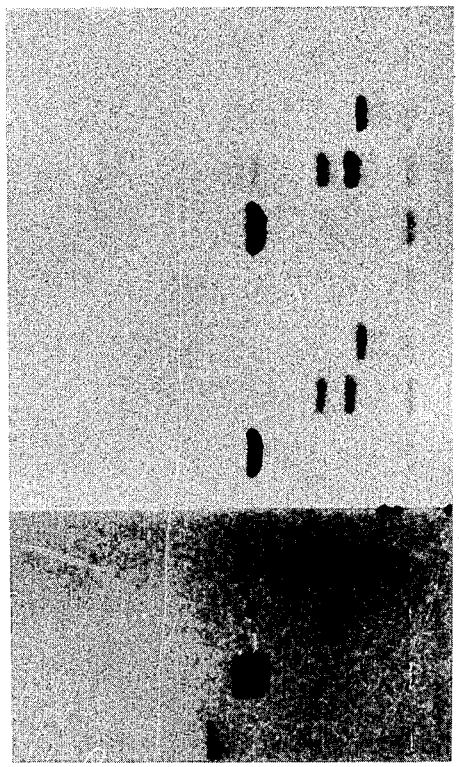
FIG. 3 shows that fucosyltransferase from normal mucosa, similar to that from human small cell lung carcinoma cells, transfers fucose in α1–3 linkage to type 2 chain structures to form mono- or poly-fucosyl derivatives.

FIG. 3. Thin layer chromatography analysis of products formed from a variety of acceptor glycolipids with type 2 chain by fucosyltransferase from normal human colonic mucosa and NCI-H69 cells. Lane 1, standard $nLc_4$; lane 2, standard $III^3FucnLc_4$; lane 3, standard $V^3FucnLc_6$; lane 4, standard $III^3V^3Fuc_2nLc_6$. Lanes 5-8 are TLC profiles of products from transfer of [$^{14}$C]fucose to the indicated glycolipid catalyzed by fucosyltransferase from normal human colonic mucosa. Lane 5, product from transfer to $nLc_4$; lane 6, product from transfer to $nLc_6$; lane 7, product from transfer to $V^3FucnLc_6$; lane 8, product from transfer to glycolipids endogenous to the enzyme fraction. Lanes 9-12 are TLC profiles of products from transfer of [$^{14}$C]fucose to the indicated glycolipid catalyzed by the solubilized enzyme from NCI-H69 cells. Lane 9, product from transfer to $nLc_4$; lane 10, product from transfer to $nLc_6$; lane 11, product from transfer to $V^3FucnLc_6$; lane 12, product from transfer to glycolipids endogenous to the solubilized enzyme. The products were synthesized as described under "Experimental Procedures" using 30 $\mu$g of acceptor glycolipid. The plate was developed in a solvent system composed of $CHCl_3:CH_3O:H_2O$, 56:38:10. Standard glycolipids were visualized by orcinol spray. The location of the $^{14}$C-labelled bands was determined by autoradiography.

Figure 4:
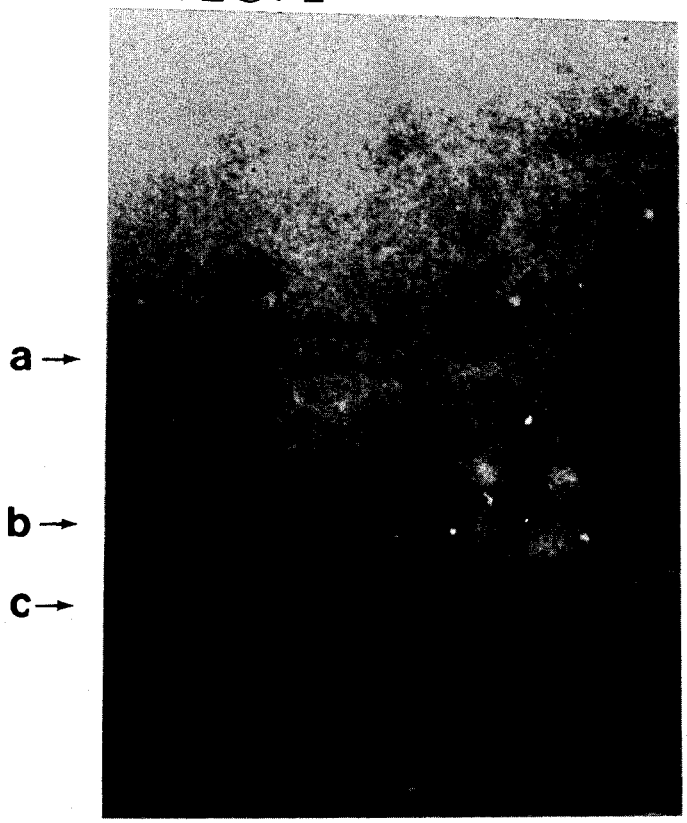
FIG. 4 shows that the fucosyltransferase from normal mucosa is indeed transferring fucose in α1–3 linkage by virtue of the formation of Le$^x$ active structures.

FIG. 4. Immunostain analysis of reaction products formed from transfer of fucose from GDPfucose catalyzed by fucosyltransferase from normal human colonic mucosa and NCI-H69 cells with the monoclonal antibody WHGS-29-1. Lane 1, standard $III^3FucnLc_4$ (a), $V^3FucnLc_6$ (b), $III^3V^3Fuc_2nLc_6$ (c); lanes 2-4 are products from transfer by enzyme from NCI-H69 cells; lane 2, product from transfer to $nLc_4$; lane 3, immunostain profile of glycolipids endogenous to the enzyme fraction; lane 4, products from transfer to $nLc_6$. Lanes 5-7 are products from transfer by enzyme from normal human colonic mucosa. Lane 5, product from $nLc_4$; lane 6, immunostain of glycolipids endogenous to the mucosal fraction; lane 7, product from transfer to $nLc_6$. The plate was developed in a solvent system composed of $CHCl_3:CH_3O:H_2O$, 56:38:10. The conditions of immunostain analysis are as described under "Experimental Procedures".

Figure 5:
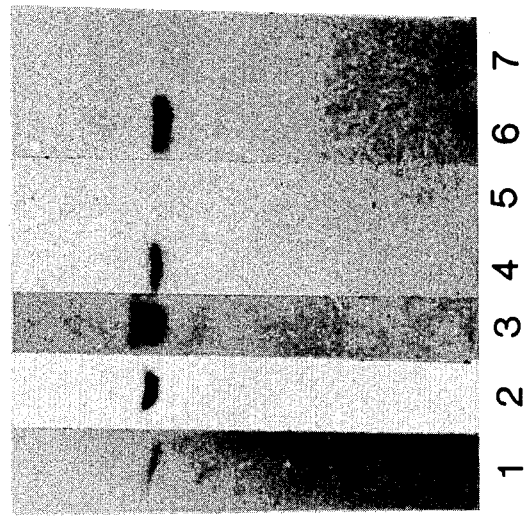
FIG. 5 shows that a β1–4galactosyltransferase is found in normal mucosa and that this enzyme can synthesize type 2 chain precursor structures.

FIG. 5. Thin layer chromatographic and immunostain analysis of products from transfer of galactose to $Lc_3$ catalyzed by enzyme fractions from NCI-H69 cells and normal human colonic mucosa. Lane 1, standard $nLc_4$; lane 2, autoradiograph of product formed from transfer of $^{14}$C-Gal to $Lc_3$ catalyzed by enzyme from NCI-H69 cells; lane 3, autoradiograph of products formed catalyzed by normal human colonic mucosa; lane 4, immunostain analysis of reaction products from transfer of galactose to $Lc_3$ by enzyme from NCI-H69 cells with antibody 1B2. Lane 5, immunostain profile of products of transfer to glycolipids endogenous to the enzyme from NCI-H69 cells; lane 6, immunostain profile of products from transfer to Lc3 catalyzed by human colonic mucosa; lane 7, immunostain profile of products from transfer to glycolipids endogenous to human colonic mucosa. The plates were developed in a solvent system composed of $CHCl_3:CH_3OH:H_2O$, (60:35:8). Standard $nLc_4$ was visualized by orcinol spray. The conditions of immunostain analysis were as described under "Experimental Procedures".

Figure 6:
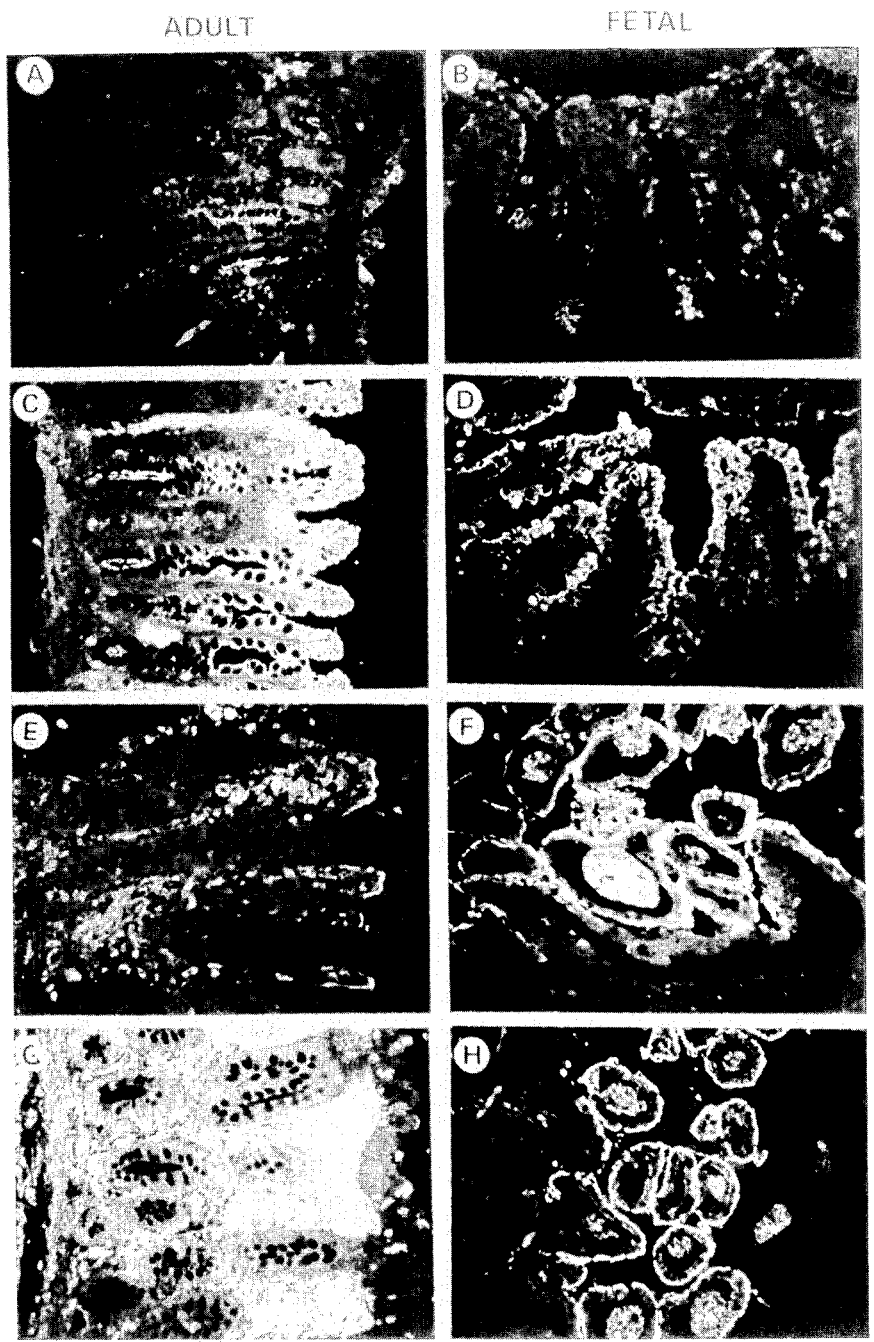
FIG. 6 shows that the co-existence in normal mucosa of β1–4galactosyltransferase and α1–3fucosyltransferase without the synthesis of Le$^x$ active structures is due to the expression of type 2 chain precursors in different cell populations of normal mucosa than those cells expressing fucosyltransferase activity.

FIG. 6. Immunofluorescence analysis of tissue sections from normal human adult and fetal proximal colon. Panels A,C,E, and G are results from adult tissues. Panels B,D,F, and H are results from fetal tissues at 120 days gestation. Panels A and B, tissue immunofluorescence with $Le^x$ specific antibody FH3 after treatment of the sections with neuraminidase. Panels C and D, tissue immunofluorescence with anti-$Le^a$ antibody after neuraminidase treatment of the sections. Panels E and F, tissue immunofluorescence with type 2 chain specific antibody 1B2 before neuraminidase treatment of the sections. Panels G and H, tissue immunofluorescence with antibody 1B2 after neuraminidase treatment of the sections. The sections were prepared as described under "Experimental Prodecures". Magnification 200×.

Figure 7:
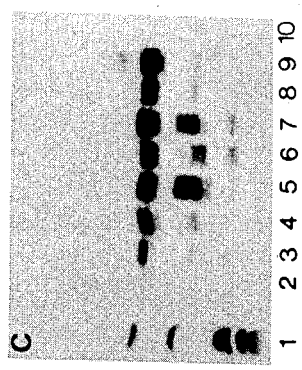
FIG. 7 shows that neutral glycolipids from normal human colonic epithelial cells contain almost no detectable type 1 or 2 chain based glycolipid antigens but that several colonic adenocarcinoma cell lines contain large quantities of these structures based on orcinol (Panel A) or immunostain analysis with specific antibodies (Panels B-G).
Figure 7:
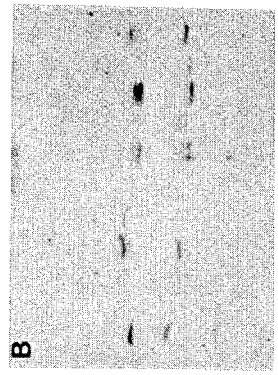
Figure 7:
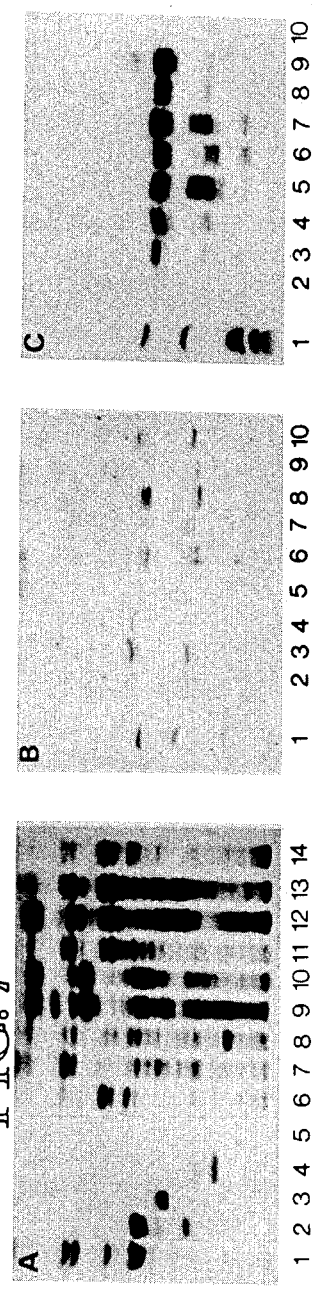
Figure 7:
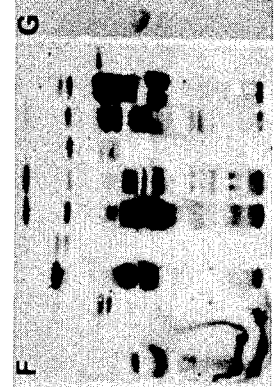
Figure 7:
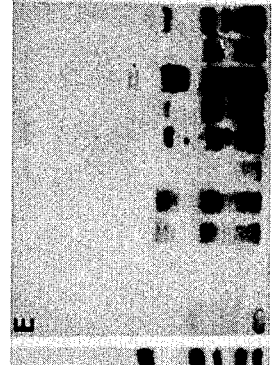
Figure 7:
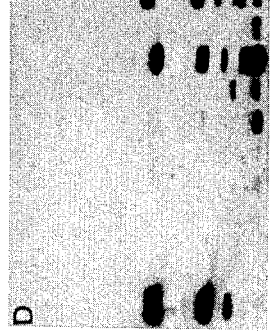
Figure 7:
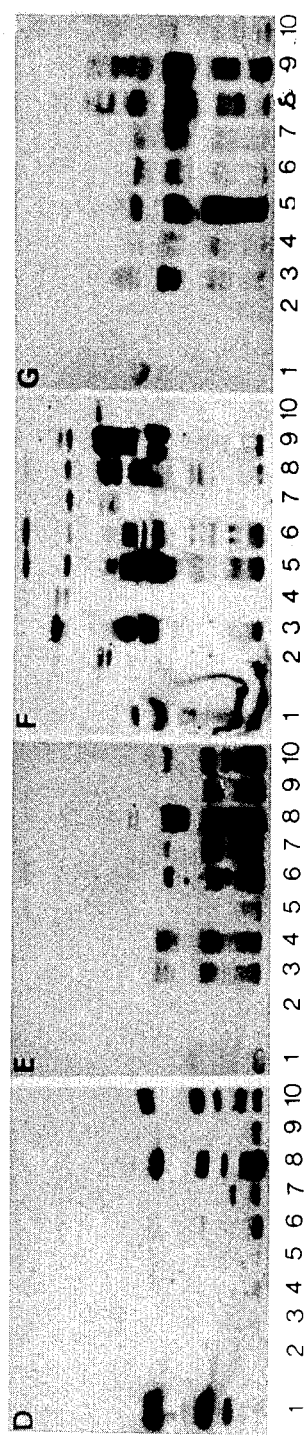

FIG. 7. High performance thin layer chromatography analysis of neutral glycolipids isolated from normal colon and colonic adenocarcinoma cell lines. Panel A: Orcinol staining. Lane 1, standard globoside ($Gb_4$), $Gb_3$, and lactosylceramide (in terms of increasing mobility); lane 2, standard $hLc_6$ and $nLc_4$ (in terms of increasing mobility); lane 3, standard $III^3FucnLc_4$; lane 4, standard $V^3FucnLc_6$; lane 5, standard $III^3V^3Fuc_2nLc_6$; lanes 6–14, neutral glycolipids from HCMC, DLD-1, HCT-15, Colo 205, SW403, SW480, SW948, SW1417, and PC9 cells, respectively. Panel B: Immunostain with 1B2 antibody. Lane 1, human type "O" whole blood cell neutral glycolipid fraction; lanes 2–10, neutral glycolipids from cell lines as described in Panel A. Panel C: Immunostain with H1B4 antibody. Lanes 1–10 are as described for Panel B. Panel D: Immunostain with WGHS-29-1 antibody. Lanes 1–10 are as described for Panel B. Panel E: Immunostain with AH6 antibody. Lanes 1–10 are as described for Panel B. Panel F: Immunostain with anti-$Le^a$ antibody. Lanes 1–10 are as described for Panel B. Panel G: Immunostain with anti-Leb antibody. Lanes 1–10 are as described for Panel B. An amount of glycolipid equivalent to that from 20 mg of packed cells was spotted in each case. The solvent system was composed of $CHCl_3:CH_3OH:H_2O$, 60:35:8.

Figure 8:
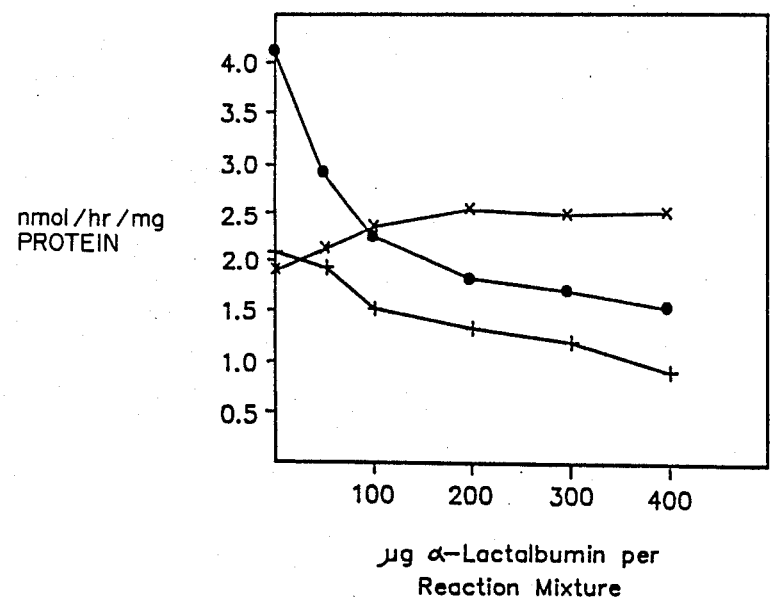
FIG. 8 shows that β1–4galactosyltransferase expressed in colon cells and associated with synthesis of type 2 chain precursor structures is also responsible for the synthesis of lactosylceramide which is common to all cells both normal and transformed and is similar to the lactose synthetase A protein.

FIG. 8. Effect of increasing α-lactalbumin on the transfer of galactose to glucosylceramide, +—+, $Lc_3$ forming $nLc_4$, •—•, and $Lc_3$ forming $Lc_4$, x—x, catalyzed by a 0.2% Triton X-100 soluble fraction from SW403 cells. The assays were conducted in the presence of 30 μg of the indicated acceptor and 0.2 mg of solubilized protein.

Figure 9:
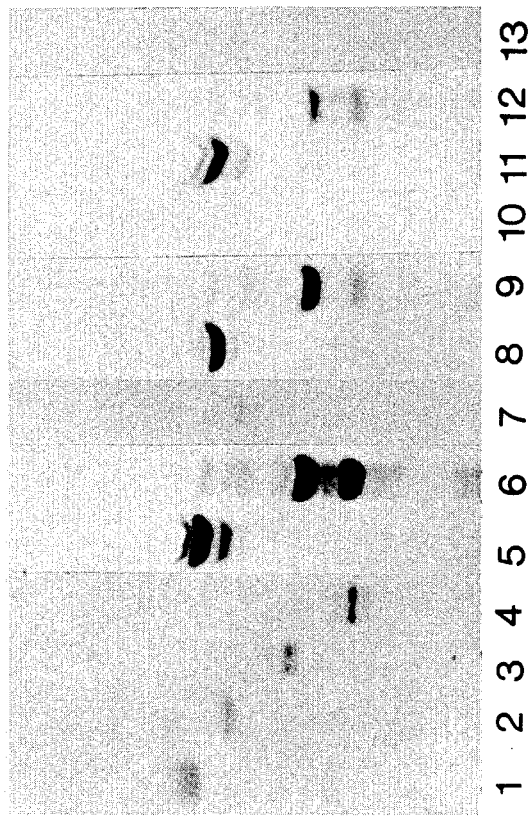
FIG. 9 shows that the fucosyltransferase activity from normal colonic epithelial cells is similar to that from adenocarcinoma cells.

FIG. 9. Thin layer chromatography profiles of fucosyltransferase products. Lane 1, standard $III^3FucnLc_4$; lane 2, standard $nLc_6$; lane 3, standard $V^3FucnLc_6$; lane 4, standard $III^3V^3Fuc_2nLc_6$; lanes 5,6, and 7, autoradiographs of $^{14}C$-labeled products from NCI-H69 cells with $nLc_4$, $nLc_6$, and endogenous acceptors, respectively; lanes 8,9, and 10, $^{14}C$-labeled products from HCMC cells with $nLc_4$, $nLc_6$, and endogenous acceptors, respectively; lanes 11,12, and 13, $^{14}C$-labeled products from SW948 cells with $nLc_4$, $nLc_6$, and endogenous acceptors, respectively. The solvent system was composed of $CHCl_3:CH_3OH:H_2O$ (60:35:8). Standard glycolipids were visualized by orcinol spray.

Figure 10:
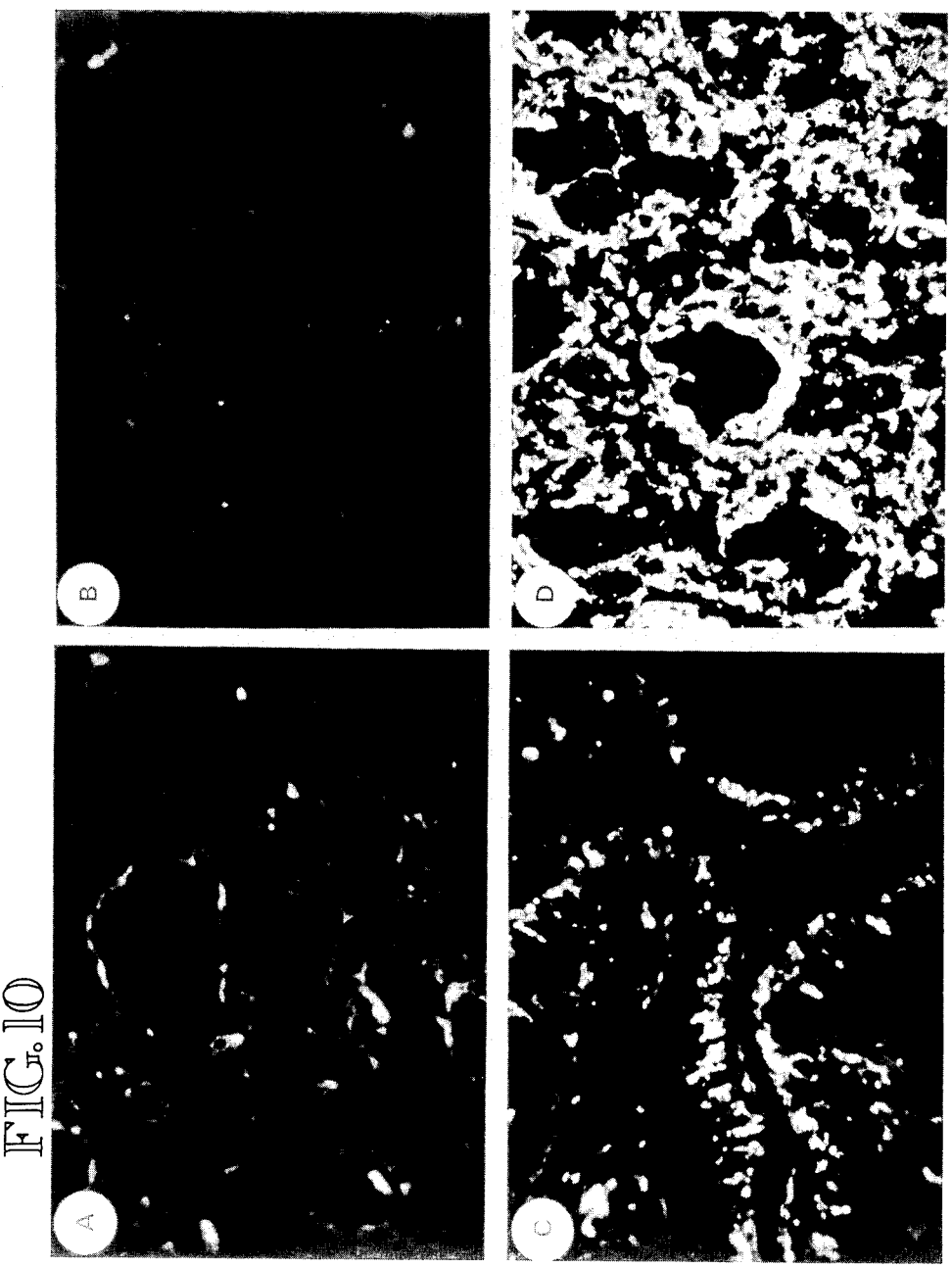
FIG. 10 shows that expression of lacto-series antigens in normal colon mucosal tissue sections can be generated by supplying the tissue with precursor acceptors and sugar nucleotide donors.

FIG. 10. In situ biosynthesis of $nLc_4$ from $Lc_3$ in tissue sections of normal adult colonic mucosa. The results shown are immunofluorescence of normal mucosal tissue sections after incubation with the N-acetyllactosaminyl residue specific antibody 1B2 followed by FITC-labelled rabbit anti-mouse secondary antibody. Panel A: Immunofluorescence of normal mucosa after pre-incubation with $Lc_3$. Panel B: Immunofluorescence of normal mucosa after incubation with a reaction mixture containing UDPGal. Panel C: Immunofluorescence of normal mucosa after pre-incubation with $Lc_3$ and incubation with a reaction mixture containing UDPGal. Panel D: Immunofluorescence of normal mucosa after pre-incubation with $nLc_4$. The sections were treated as described under "Experimental Procedures". Magnification 400×.

Figure 11:
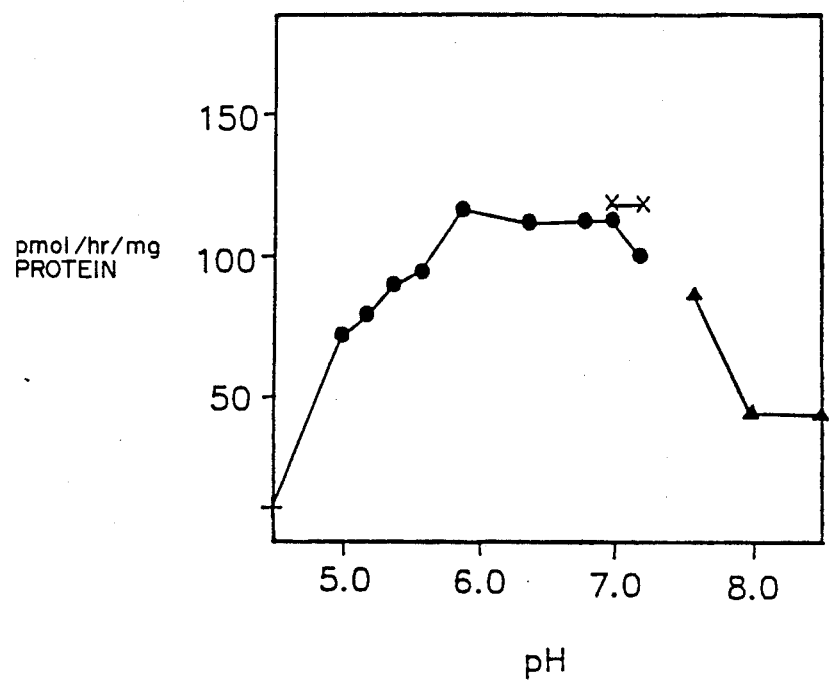
FIG. 11 shows the effect of pH on β1–3N-acetylglucosaminyltransferase activity.

FIG. 11. Effect of buffer and pH on SW403 cell β1-3N acetylglucosaminyltransferase activity. The buffers used are acetate, +—+, cacodylate, •—•, HEPES, ×—×, and Tris-HCl, FIG. 12. Hanes-Woolf plot of saturation data from SW403 cell β1-3N-acetylglucosaminyltransferase obtained by varying the concentration of acceptors $nLc_4$, •—•, and $nLc_6$, ×•×, from 32 μM to 640 μM in the presence of 0.4 mg protein and 50 nmol of $UDP[^{14}C]GlcNAc$ per 0.05 ml reaction mixture (Panel A), and by varying the concentration of UDPGlcNAc from 65 μM to 1625 μM in the presence of 0.4 mg protein and 750 μM lactosylceramide (Panel B).

FIG. 13. Effect of increasing time and protein on β1-3N-acetylglucosaminyltransferase activity. Panel A: Time course of transfer reaction. The standard reaction mixture was scaled up 6-fold in the presence of 2.4 m8 protein. Aliquots, 0 05 ml each were withdrawn at the times indicated and the incorporation of labelled GlcNAc into lactosylceramide was quantitated. Panel B: Effect of increasing protein concentration. The conditions were the same as described under "Experimental Procedures" except that the solubilized protein was varied from 100 to 500 μg per reaction mixture.

Figure 14F:
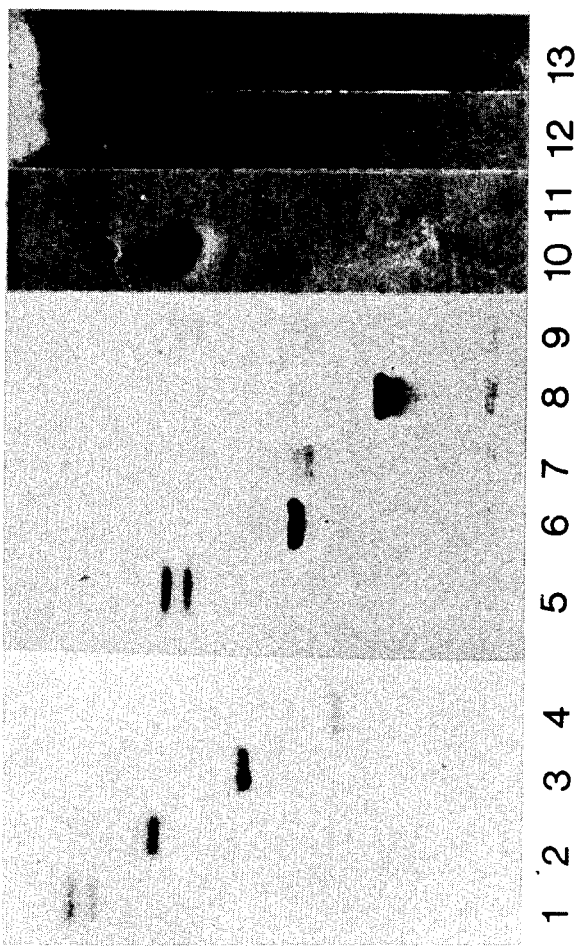
FIG. 14 shows that the β1–3N-acetylglucosaminyltransferase will transfer GlcNAc to structures containing a terminal galactose residue only if it is not derivatized by addition of other sugars such as fucose.

FIG. 14. High performance thin layer chromatographic analysis of β1-3N-acetylglucosaminyltransferase reaction products. Lane 1, standard lactosylceramide; lane 2, standard $Lc_3$; lane 3, standard $nLc_4$; lane 4, standard $nLc_6$; lane 5, autoradiograph of product from transfer of $[^{14}C]$-GlcNAc to lactosylceramide; lane 6, autoradiograph of product from transfer[to $nLc_4$; lane 7, autoradiograph of product from transfer to $Lc_4$; lane 18, autoradiograph of product from transfer to $nLc_6$; lane 9, autoradiograph of products from transfer to endogenous acceptors; lane 10, immunostain analysis with antibody J1 with standard $Lc_3$; lane 11, immunostain analysis of acceptor lactosylceramide; lane 12, immunostain analysis of product from transfer of unlabelled GlcNAc to lactosylceramide; lane 13, immunostain analysis of products from transfer to endogenous acceptors. Standard glycolipids were visualized by orcinol spray. The solvent system was composed of $CHCl_3:CH_3OH:H_2O$, 60:35:8.

FIRST SERIES OF EXAMPLES

The expression of a wide diversity of lacto-series antigens has been described to be associated with colonic adenocarcinomas. The nature of the control of the synthesis of these antigens in normal compared to premalignant or malignant tissues is essential to the understanding of this phenomenon and a key for use of these markers for diagnostic purposes.

To determine the nature of the expression of lacto-series carbohydrate antigens during oncogenesis in human tissues, normal human colonic mucosa was studied to determine its enzymatic content of glycosyltransferases associated with lacto-series chain synthesis and its level of expression of lacto-series carbohydrate chains. Reported here is data which indicates that normal human adult mucosa contains the glycosyltransierase activities necessary to synthesize the tumor-associated $Le^x$ series of antigens, however, they are not formed.

Data shows that the colonic mucosal epithelial cells (the precursor cells to colonic adenocarcinomas) in adult tissues are unable to synthesize type 2 lacto-series core chains thus preventing the expression of type 2 chain based tumor-associated antigens such as $Le^x$. Alteration of expression of type 2 core chains is thus the essential feature in expression of all type 2 chain based tumor-associated antigens in colonic adenocarcinomas.

EXAMPLE 1

Glycolipid pattern in normal human colonic mucosa and colonic adenocarcinomas.

The glycolipid composition from cells of normal adult colonic mucosa was analyzed and compared with that from colonic adenocarcinoma tumors to demonstrate the qualitative differences between them along with the complexity of tumor-associated antigens present in tumor tissue.

Analysis of the glycolipid composition was performed by immunostain procedures utilizing specific antibodies with glycolipid fractions isolated from pooled mucosal tissue. Scraped mucosal tissue is comprised of epithelial cells as well as connective tissue and various inflammatory cells. The glycolipid profiles of normal colonic mucosa were compared with those of the human small cell lung carcinoma cell line NCI-H69 cells and human colonic adenocarcinoma tumors and shown in FIG. 1. The greatest chemical quantity of neutral glycolipids isolated from normal mucosal tissue migrates in the area of CDH and $Gb_3$. Minor bands are also observed that migrate with tetraglycosylceramide and longer chain derivatives (FIG. 1A, lane 6). In contrast, most of the glycolipid bands isolated from NCI-H69 cells and human adenocarcinoma tumors FT-620 and TG-115 are slower migrating components (lanes 7–9). FIG. 1b shows results of immunostain analysis with the $Le^x$ determinant specific antibody WGHS-29-1. A similar pattern of bands is observed for glycolipids extracted from NCI-H69 cells and human colonic adenocarcinoma tumors FT-620 and TG-115 known to accumulate large quantities of $Le^x$ determinant carrying structures (lanes 5–7). In these glycolipid fractions, intense bands corresponding to $III^3FucnLc_4$, $V^3FucnLc_6$, $III^3V^3Fuc_2nLc_6$, and slower migrating bands are observed in each fraction. Many of these bands are normally found in small quantities in extracts from type "O" whole blood from leukocytes or normal human liver as shown in lanes 2 and 3, respectively. Only very weak reactive glycolipid bands are found in extracts of normal colonic mucosa that co-migrate with $III^3V^3Fuc_2nLc_6$ and a slower migrating band. No staining of faster migrating bands is observed. Immunostain analysis with the $Le^y$ specific antibody AH6 indicated no staining of glycolipids from normal mucosal fractions (results not shown). These results indicate that almost no $\alpha 1$-3 fucose containing structures are present in the neutral glycolipid fraction of normal colonic mucosa. Immunostain analysis with antibody 1B2, specific for type 2 chain structures $nLc_4$, $nLc_6$, $nLc_8$, etc., is shown in FIG. 1c. Bands corresponding to $nLc_4$, $nLc_6$, and longer chain structures are found in the neutral glycolipid fractions of NCI-H69 cells, FT-620, and TG-115 (less 5–7). But with normal colonic mucosa, only a weak band corresponding to $nLc_6$ is found (lane 4).

Type 1 chain fucosylated derivatives were readily-detected with anti-$Le^a$ antibody (FIG. 1d). Strong staining corresponding to $III^4FucLc_4$ is found in the glycolipid fraction from type "O" RBC's (lane 2), FT-620 (lane 6), and TG-115 (lane 7). In addition, strong staining is also found corresponding to $III^4FucLc_4$ and a slower migrating band in the glycolipid fraction of normal colonic mucosa (lane 4) indicating the presence of type 1 chain containing structures.

These results indicate that only a small quantity of type 2 chain structures, either fucosylated or non-fucosylated, are found in the neutral glycolipid fraction from normal colonic mucosa. Identification of type 2 chain structures present in the 8anglioside fraction from normal mucosa was performed with antibody 1B2 after desialylation with 1% acetic acid at 100° C. for 1 hour. These results are shown in FIG. 2. Staining of multiple bands corresponding to $nLc_4$, $nLc_6$, and slower migrating glycolipids is observed after hydrolysis of standard type "O" RBC gangliosides (lane 2), and of a band corresponding to $nLc_4$ and weak slower migrating bands with hydrolyzed gangliosides from NCI-H69 cells (lane 3). In addition, bands corresponding to $nLc_4$ and $nLc_6$ and a weaker slower band are found with hydrolyzed gangliosides from normal colonic mucosa (lane 4). Previous results (J. Biol. Chem., 261, 3737–3743 (1986)) have indicated that gangliosides based on type 2 chains can be fucosylated to yield sialyl-$Le^x$ derivatives. Immunostain analysis of the desialylated gangliosides from normal colonic mucosa using the $Le^x$ determinant specific antibody WGHS-29-1 was negative indicating the absence of sialyl $Le^x$ structures in this fraction (results not shown). These results indicate that type 2 lacto-series chains are present in normal colonic mucosa in very low quantity and that almost all of these type 2 chain based glycolipids in the normal colonic mucosa are present as either $\alpha 2$-3 or $\alpha 2$-6 sialyl derivatives.

EXAMPLE 2 $\alpha 1$-3Fucosyltransferase activity of NCI-H69 cells and normal human colonic mucosa.

One of the most commonly observed tumor-associated carbohydrate antigens found in adenocarcinomas is the $Le^x$ antigen. This is actually a series of structures containing $\alpha 1$-3 linked fucose residues on GlcNAc residues of type 2 lacto-series core chains. The $\alpha 1$-3 linked fucose on GlcNAc is also found on other more complex type 2 chain derivatives such as $Le^y$ structures and sialyl $Le^x$ structures. Essentially all of these $\alpha 1$-3 fucosyl derivatives have been described as being tumor markers or markers of premalignant tissues. The common feature of $\alpha 1$-3 fucosyl residues has drawn attention to the $\alpha 1$-3fucosyltransferase whose activation might be the enzymatic lesion responsible for induction of these $\alpha 1$-3 fucosyl structures in adenocarcinomas. To investigate this further, the $\alpha 1$-3fucosyltransferase activity was studied in normal mucosa and compared to that from NCI-H69 cells which accumulate large quantities of α1-3 linked fucose structures.

TABLE 1

α1→3 Fucosyltransferase activity of crude homogenates of NCI-H69 cells and normal human colonic mucosa.

| Extract Source | pmol/hr/mg protein |
| --- | --- |
| NCI-H69 cells | 720. ± 20 |
| Normal colonic mucosa case #1 | 167. ± 11 |
| Normal colonic mucosa case #2 | 299. ± 14 |
| Normal colonic mucosa case #3 | 199. ± 12 |

Assays were performed as described under "Experimental Procedures" Using nLc$_4$ as the acceptor glycolipid. The variation between duplicate determinations is shown.

Table 1 shows a comparison of the α1-3 fucosyltransferase specific activity of crude homogenates from normal human colonic mucosa and the human small cell ling carcinoma cell line NCI-H69 with nLc$_4$ as the acceptor. Although the fucosyltransferase activity is highest in NCI-H69 cells, there is significant activity present in the scraped mucosal fraction where the specific activity of the different cases is decreased only 2- to 4fold. FIG. 3 shows results of incorporation of $^{14}$C-fucose into acceptor nLc$_4$, nLc$_6$, and V$^3$Fucnlc$_6$ catalyzed by normal mucosal and NCI-H69 cellhomogenates. These results show that the TLC mobility of reaction products after transfer of $^{14}$C-fucose to nLc$_4$, nLc$_6$, or V$^3$FucnLc$_6$ by homogenates of NCI-H69 cells (lanes 9-12) is identical to results obtained when homogenates of normal mucosa were used as the enzyme source (lanes 5-8). Results of immunostain analysis of parallel reaction products after transfer of unlabelled fucose to acceptor nLc$_4$ and nLc$_6$ using the Le$^x$ determinant specific antibody WGHS-29-1 is shown in FIG. 4. The same pattern of staining is observed for normal mucosal reaction products (lanes 5-7) and NCI-H69 cell products (lanes 2-) with the indicated acceptor glycolipids. In addition, these bands correspond to the products formed from transfer of $^{14}$C-fucose indicating that all of the products detected are α1-3 linked. Immunostain analysis of the reaction products with the H-specific antibody BE2 indicated no evidence for formation of α1-2 linked fucose structures (results not shown).

These results show that significant α1-3fucosyltransferase activity is found in normal colonic mucosa despite the lack of α1-3 fucose containing carbohydrate structures i the glycolipids extracted from normal mucosa as demonstrated in Example 1 above. The α1-3 fucosyltransferase from normal mucosa was investigated further as shown below.

Nature of the fucosyltransferase from normal adult colonic epithelia

Both α1-3 (J. Biol. Chem., 260, 7619-7627 (1985), Eur. J. Biochem., 30, 269-277 (1972), Eur. J. Biochem., 130, 347-351 (1983)) and α1-¾(J. Biol. Chem., 256, 10456-10463 (1981), Biochem. Biophys. Res. Commun., 100, 1611-1618 (1981),FEBS Lett., 142. 77-80 (1982)) specific fucosyltransferases have been identified in human cells. The nature of this activity in normal colonic epithelia was determined by kinetic analysis of the reaction with different acceptor substrates. Table 2 shows the incorporation of $^{14}$C-fucose into either Lc$_4$, nLc$_4$, or mixed Lc$_4$ and nLc$_4$ catalyzed by enzyme fractions from NCI-H69 cells which contain a highly specific α1-3fucosyltransferase and normal colonic mucosa. The results indicate that a single α1-3 specific fucosyltransferase is found in NCI-H69 cells consistent with previous results (J. Biol. Chem., 260, 7619-7627 (1985)). Enzyme activities catalyzing transfer to both Lc$_4$ and nLc$_4$ are found in normal mucosal fractions. The activity with nLc$_4$ as acceptor yielded about 2-fold higher activity than when Lc$_4$ was the acceptor. This is essentially the same result previously found for the Le-gene specified fucosyltransferase from human milk (J. Biol. Chem., 256,10456-10463 (1981)). Analysis of the activity when both Lc$_4$ and nLc$_4$ are mixed indicates that essentially all of the fucosyltransferase activity can be accounted for by a single enzyme, most probably the Le-gene specified fucosyltransferase, capable of transferring fucose in either α1-3 or α1-4 linkages.

TABLE 2

Substrate competition studies with fucosyltransferases from homogenates of NCI-H69 cells and normal human colonic mucosa

| | pmol [$^{14}$C] fucose transferred/hr/mg protein to: | | | calculated values for: | |
| --- | --- | --- | --- | --- | --- |
| Enzyme Source | Lc$_4$ | nLc$_4$ | Lc$_4$ + nLc$_4$ | One enzyme | Two enzymes |
| NCI-H69 cells | ND | 1208. | 1195. | | |
| Normal colonic mucosa case #1 | 83. | 297. | 177. | 179. | 380. |
| Normal colonic mucosa case #2 | 270. | 551. | 418. | 386. | 821. |
| Normal colonic mucosa case #3 | 95. | 210. | 158. | 144. | 305. |

Reaction mixtures were as described under "Experimental Procedures" and contained 40 μg of Lc$_4$, nLc$_4$, or 40 μg of both Lc$_4$ and nLc$_4$. Data is shown for a single experiment. The results were reproducable with less than 5% variation between experiments. Calculated values for activity with mixed acceptor composition were determined using the following equations. Terms of the equations are defined as follows. $v_t$=total velocity; $v_a$=velocity of transfer to acceptor Lc$_4$; $v_b$=velocity of transfer to nLc$_4$; $V_a$=miximal velocity of transfer to Lc$_4$; $V_b$=maximal velocity of transfer to nLc$_4$; a=concentration of Lc$_4$; b=concentration of nLc$_4$; $K_a$=$K_m$ for Lc$_4$; $K_b$=$K_m$ for nLc$_4$.

$$\text{Two enzymes } v_t = v_a + v_b$$

$$\text{One enzyme } v_t = \frac{V_a a/K_a + V_b b/K_b}{1 + a/K_a + b/K_b}$$

ND = none detected

This indicates that expression of α1-3 fucose containing structures in both normal colonic mucosa and in derived adenocarcinomas is regulated by the Le-gene and thus depends on the Lewis blood group status of the individual. This has already been shown for type 1 chain based Le$^a$ antigens which also accumulate in adenocarcinomas (see Example 6 for discussion of type 1 chain based antigens). Additionally, this data indicates that expression of fucosyltransferase activity is independent of synthesis of α1-3 linked fucose containing tumor-associated carbohydrate antigens.

EXAMPLE 3

UDPgalactose:Lc$_3$ galactosyltransferase activity of normal colonic mucosa and NCI-H69 cells.

To understand the basis for the expression of type 2 chain lacto-series antigens in adenocarcinomas, information relating to the biosynthetic capacity of normal mucosa and adenocarcinoma tumors for type 2 core structures is necessary. This was investigated by determining the enzyme activity associated with type 2 chain synthesis from its immediate precursor Lc$_3$ which is also the precursor of type 1 chain based antigens which have been found on normal mucosal epithelial cells. This enzyme is a β1–4galactosyltransferase and was studied as shown below.

TABLE 3

UDPGalactose:Lc$_3$ Galactosyltransferase activity of NCI-H69 cells and normal human colonic mucosa.

| Enzyme Source | pmol galactose transferred/hr/mg protein | |
|---|---|---|
| | as Lc$_4$ | as nLc$_4$ |
| NCI-H69 cells | ND | 567. ± 10 |
| Normal colonic mucosa case #1 | 300. ± 7 | 459. ± 8 |
| Normal colonic mucosa case #2 | 432. ± 8 | 772. ± 17 |
| Normal colonic mucosa case #3 | 280. ± 5 | 445. ± 9 |

The enzyme reactions were performed as described under "Experimental Procedures", using crude homogenates as enzyme sources. Variation between duplicate determinations is shown. ND=none detected The results of transfer of $^{14}$C-galactose to Lc$_3$ catalyzed by fractions from normal colonic mucosa and NCI-H69 cells is shown in FIG. 5 and Table 3. A single labelled band which co-migrates with nLc$_4$ is found after transfer by enzyme from NCI-H69 cells (FIG. 5, lane 2). In the case of the normal colonic mucosa, a band that co-migrates with nLc$_4$ is found and in addition a faster migrating band is observed (lane 3). Identification of these bands by immunostain analysis by antibody 1B2 after transfer with unlabelled galactose indicates that the single product formed by NCI-H69 cells and the slower migrating band in the mucosal fraction is nLc$_4$ (FIG. 5, lanes 4 and 6, respectively). This was confirmed by isolating the individual $^{14}$C-labelled bands from each reaction mixture and TLC analysis of each band after acetylation. Results indicate that the single band from NCI-H69 cells and the slower band from the mucosal fractions co-migrate as acetylated derivatives with nLc$_4$. The faster migrating band in the mucosal fractions co.migrates with standard Lc$_4$ as acetylated derivatives (results not shown). The quantitative incorporation of $^{14}$C-galactose into each product is shown in Table 3. Approximately 60 to 65% of the $^{14}$C-galactose transferred to Lc$_3$ is incorporated into nLc$_4$.

The results indicate that normal colonic mucosa has significant activity of both a β1–4galactosyltransferase and an α1-3fucosyltransferase. These enzymes are required for synthesis of type 2 chain core structures and fucosylated derivatives. Despite the level of expression of the α1-3fucosyltransferase, almost all of the type 2 chain structures found in normal colonic mucosa were sialylated derivatives and were not converted to either Le$^x$ or sialyl-Le$^x$ determinant structures. The lack of expression of fucosylated derivatives in the presence of significant fucosyltransferase activity and β1–4galactosyltransferase activity was investigated further as shown in the next example below.

EXAMPLE 4

Tissue immunofluorescence studies of normal adult proximal colon and fetal intestine To determine the reason for the lack of expression of large quantities of type 2 chain structures and their fucosylated derivatives in normal mucosa the tissue localization of these carbohydrate structures was studied in normal adult colon tissue and in human fetal colon tissue. Fetal colon tissue has been shown to express type 2 chain fucosylated antigens similar to colonic adenocarcinomas. The expression of these antigens has thus been described as onco-fetal in nature. For this reason, fetal colon tissue is a good comparative tissue to study expression of these carbohydrate antigens in relation to both developmental and oncogenic changes.

Results presented in FIG. 6 indicate the comparative expression of carbohydrate antigens in normal adult proximal colon and in proximal portions of fetal colon tissue. Panels A and B demonstrate the binding of FH3 antibody specific for Le$^x$ antigens (*J. Biol. Chem.*, 259, 4681–4685 (1984)) in neuraminidase treated adult and fetal colon tissue, respectively. In agreement with previously reported data (*J. Exp. Med.*, 159, 506–520 (1984)), almost no staining is observed in adult tissue whereas significant staining is observed in crypt cells and the epithelial cell layer of fetal colon tissue. Similar results were obtained with tissue sections without neuraminidase treatment except that the staining intensity of fetal tissue was less indicating the presence of some sialyl-Le$^x$ in this tissue (*Cancer Res.*, 45, 3711–3717 (1985), *Cancer Res.*, 44, 5279–5285 (1984)) (results not shown). Panels C and D show results of tissue staining with antibody specific for type 1 chain based Le$^a$ antigens after treatment with neuraminidase. Intense staining of crypt cells and epithelial cells of both adult and fetal tissue is observed. This is consistent with similar results previously reported (*Lab. Invest.*, 50, 394–400 (1984), *Cancer Res.*, 45, 4499–4511 (1985)) and indicate the presence of a fucosyltransferase associated with synthesis of Le$^a$ structures from type 1 chain precursors in the epithelial cell layer of both fetal and adult proximal colon tissue. Panels E and F show results of staining with antibody specific for type 2 chain structures nLc$_4$, nLc$_6$, etc. prior to neuraminidase treatment of the tissue sections. Essentially no staining of adult epithelial cells was observed. Virtually all staining occurred in the lamina propria of adult mucosa where infiltrative cells are stained (*J. Biol. Chem.*, 260. 1067–1082 (1985), *J. Immunol.*, 134, 2498–2506 (1985)) (Panel E). In contrast, intense staining is observed in the epithelial cell layer of fetal tissue (Panel F). This result is further magnified after neuraminidase treating the tissue sections reflecting the abundance of gangliosides in these cells. Panels G and H show these results. Staining in adult lamina propria is much more intense and is still absent from the layer of epithelial cells (Panel G). Staining of cells of fetal colon is again limited to cells of the epithelium. Thus, the small quantity of type 2 chain structures detected in normal mucosa as described in previous sections is most probably due to contamination of the epithelial cells with leukocytes. These results indicate that type 2 chain structures nLc$_4$, nLc$_6$, etc. are expressed in epithelial cells of fetal colon but not in epithelial cells of adult tissue. Fucosylated derivatives are restricted to epithelial cells. These results strongly suggest that the 1-¾ fucosyltransferase activity and synthesis of type 2 core chains are properties of different cell populations of normal colonic mucosa. Oncofetal expression of all type 2 chain based antigens which occur in fetal colonic epithelia and adult colonic adenocarcinomas is most probably due to the retrogenetic expression of type 2 chain core structures which are normally absent in adult colonic epithelial cells.

DISCUSSION

The results presented in Examples 1 to 4 indicate that expression of type 2 chain structures in general and $Le^x$ antigen structures in particular are onco-developmental in nature. This means that these carbohydrate structures are normally expressed during certain stages of normal development, regress greatly in adult tissues, and reappear in association with oncogenesis. Similar results have been obtained from a developmental aspect in mouse embryos where $Le^x$ structures appear during the 8 to 16 cell stage and regress after the 32 cell stage (*Proc. Natl. Acad. Sci. U.S.A.*, 75, 5565–5569 (1978)). This implies a functional role for this carbohydrate structure during development which is also important during oncogenesis. As a consequence of this, changes in the carbohydrate composition of colon cells may be an early indicator of oncogenesis and thus have diagnostic value. Evidence for this has been obtained for the $Le^y$ determinant which also carries an α1-3 linked fucose residue on a type 2 lacto-series chain (*Cancer Res.*, 46, 2639–2644 (1986), Cancer Res., 46, 5985–5992 (1986)). The expression of the $Le^y$ determinant on colonic polyps showing greater dysplasia was noted. This antigen is also common in colonic adenocarcinomas.

The potential functional significance of these types of carbohydrate antigen changes in oncogenesis and the resulting value for diagnosis is clouded by the great diversity of antigens found in actual colonic adenocarcinomas. No single structure or monoclonal antibody generated against a given structure has been shown to be specific for all adenocarcinoma tumors. This has limited the use of these antigens and antibodies against these structures in diagnostic applications. Therefore, it would be of considerable importance to determine the specific enzymatic lesion or lesions which are responsible for the formation of these antigens in premalignant tissues and tumors and base diagnostic procedures on a more common expression or mechanism of activation of antigen expression. In order to determine this, information has been gained to isolate this lesion or lesions.

As indicated in Examples 1 to 4, alteration of expression of an α1-3fucosyltransferase does not correlate with fucosylated type 2 lacto-series chain expression. In fact, this activity in normal mucosa is associated with a fucosyltransferase with dual specificity as an α1-¾fucosyltransferase which can transfer fucose to either type 1 or 2 lacto-series chains. This enzyme is associated with the expression of the Le-gene of the Lewis blood group. This is found to be normally expressed in secretory tissues of man, although the extent of accumulation of chemical quantities of these structures is low compared to tumor tissues.

Also shown in Examples 1 to 4 are results which indicate that type 2 lacto-series core chains are not found in epithelial cells of normal adult colonic mucosa although fucosyltransferase activity is expressed in these cells. Type 2 lacto-series core chains were found in fetal colonic epithelial cells. This indicates that expression of type 2 chain based antigens in adenocarcinomas is regulated through activation of synthesis of type 2 chain core structures in epithelial cells of colonic mucosa. The specific enzymatic lesion associated with activation of type 2 lacto-series core chain synthesis in colonic epithelial cells was investigated and is described in the next series of Examples.

SECOND SERIES OF EXAMPLES

To determine the specific enzymatic lesion responsible for the regulation of synthesis of type 2 lacto-series core chains, a series of investigations were performed using tissue culture cell lines of normal adult colonic mucosal epithelial cell origin and several human colonic adenocarcinoma cell lines. Using these cell lines comparative aspects of the normal cells and tumor cells can be obtained without contamination from other cell types as with scraped colonic mucosa.

EXAMPLE 5

Analysis of glycolipids isolated from normal mucosal and colonic adenocarcinoma cell lines To determine the nature of carbohydrate structures on glycolipids of normal colonic epithelial cells and adenocarcinomas from cell lines in comparison with results presented in Example 1 above, the following studies were undertaken.

FIG. 7 shows results of glycolipid analysis by orcinol staining and TLC immunostain analysis. It is apparent by orcinol staining that only the transformed cell lines contain significant quantities of slower migrating, long chain glycolipid bands (Panel A, lanes 7–14). The normal mucosal epithelial cell line, HCMC, contain almost no longer chain glycolipids, the major bands co-migrating with $Gb_3$ and $Gb_4$ (lane 6). These results are equivalent to those obtained with glycolipids extracted from colonic adenocarcinoma tumors (*J. Biol. Chem.*, 259, 4672–4680 (1984)).

The nature of the glycolipids found in these cells was further studied by TLC immunostain analysis. Panel B shows results with the type 2 chain N-acetyllactosaminyl residue specific antibody 1B2. Staining of bands co-migrating with $nLc_4$ and/or $nLc_6$ is observed in each of the adenocarcinoma cell lines (lanes 3–10), although weak staining is found with Colo 205 cells. Weak staining is also observed with HCMC cells where only $nLc_6$ is detectable. Type 2 core chains are the biosynthetic intermediate for a variety of fucosylated derivatives.

These structures H, $Le^x$, and $Le^y$ antigens defined by specific monoclonal antibodies is shown in Panels C, D, and E, respectively. The major H-antigen defined by H1B4 antibody in all colonic adenocarcinoma cell lines corresponds to $H_1$ ($IV^2FucnLc_4$) and $H_2$ ($VI^2FucnLc_6$). Lung carcinoma cell line PC9 did not show the presence of H-antigen. All the adenocarcinoma cell lines, with the exception of Colo 205 (lane 5) showed typical multiple bands for $Le^y$ structure. In contrast to $Le^y$, only a few cell lines, SW948 and PC9, showed a strong staining with WGHS-29-1 antibody, which is directed to $Le^x$ structure. Neither H, $Le^x$, nor $Le^y$ were detectable in neutral glycolipid from HCMC normal mucosal cells. The abundance of multiple $Le^y$ active compounds also was found in various human colonic adenocarcinomas and the pattern is essentially the same as described in these colonic adenocarcinoma cell lines. The major bands correspond to $III^3IV^2Fuc_2nLc_4$, $V^3VI^2Fuc_2nLc_6$, and $III^3V^3VI^2Fuc_3nLc_6$, respectively.

The glycolipid patterns of each cell line, immunostained by type 1 chain based anti-Le$^a$ and anti-Le$^b$ antibodies, are shown in Panels F and G (FIG. 7), respectively. A variety of non-specifically stained bands are present which migrate faster than the Le$^a$ pentasaccharide standard, the fastest migrating band shown in lane 1 of Panel F. Specific staining is observed for glycolipid components of the cell lines which correspond to penta, hepta, or longer chain structures with the anti-Le$^a$ antibodies. Interestingly, all tumor cell lines showed a series of Le$^b$ active glycolipids while normal mucosal cell line HCMC did not show the presence of an Le$^b$ active component.

A more complete summary of TLC immunostain results is shown in Table 5 using a variety of monoclonal antibodies whose specificities are described in Table 4. These results indicate that both neutral glycolipids and gangliosides based on type 1 and 2 lacto-series chains accumulate in colonic adenocarcinoma cell lines and these structures are either weak or not expressed in normal mucosal epithelial cells.

14. Brockhaus, et al, *Arch. Biochem. Biophys*, 217, 647–651 (1962).
16. Fukushi, et al, *J. Biol. Chem.*, 259, 10511–10517, (1984).
18. Abe, et al, *J. Biol. Chem.*, 258, 11793–11797, (1983).
50. Symington, et al, *Mol. Immunol.*, 21, 877–882, (1984).
51. Young, et al, *J. Exp. Med.*, 150, 1008–1019, (1979).
52. Nudelman, et al, *Science*, 220, 509–511, (1983).
53. Young, et al, *J. Biol. Chem.*, 10967–10972, (1981).
54. Young, et al, *J. Biol. Chem.*, 258, 4890–4894, (1983).
55. Blaszczyk, et al, *Arch. Biochem. Biophys.*, 233, 161–168, (1984).

TABLE 5

Summary of TLC Immunostain Results with Neutral Glycolipids and Gangliosides Isolated from Normal Colonic Mucosal and Colonic Adenocarcinoma Cell Lines Glycolipid Presence or Absence

| Cell Line | Gb$_3$ | Lc$_3$ | Gg$_3$ | Type 2 Chain | Le$^x$ | Le$^y$ | H Antigens Types 1 & 2 | H Antigens Type 2 | Le$^a$ | Le$^b$ | Sialyl Le$^x$ | Sialyl Le$^a$ |
|---|---|---|---|---|---|---|---|---|---|---|---|---|
| HCMC (O)$^a$ | ++ | − | − | +$^{c,d}$ | − | − | +$^d$ | − | +$^d$ | − | − | − |
| DLD-1 (O) | − | − | − | ++ | +$^d$ | ++ | + | + | +++ | ++ | − | +++ |
| HCT-15 (O) | + | − | − | + | +$^d$ | ++ | ++ | + | +$^d$ | + | − | − |
| Colo 205 (O)$^b$ | + | − | − | +$^d$ | − | +$^d$ | +++ | +$^d$ | +++ | +++ | − | +++ |
| SW403 (O) | +$^d$ | − | − | + | + | ++ | +++ | + | ++ | + | − | +$^d$ |
| SW480 (A) | ++ | − | − | +$^c$ | +$^e$ | ++ | +++ | + | +$^d$ | + | − | +$^d$ |
| SW948 (O) | ++ | − | − | + | ++ | ++ | ++ | + | ++ | +++ | + | +++ |
| SW1417 (B) | ++ | − | − | +$^c$ | − | + | ++ | − | ++ | +++ | − | +++ |
| PC9 (O)$^b$ | + | − | − | + | ++ | ++ | + | + | − | − | + | − |

The presence or absence of bands staining with appropriate antibodies is given.
−, not detected;
+, detectable but may be weak;
++, moderate staining;
+++, strong staining
$^a$blood type of donor individual;
$^b$blood type of donor individual deduced from TLC immunostain results (i.e. negative with monoclonal antibodies against A or B structures);
$^c$mainly nLc$_6$ staining;
$^d$very weak staining;
$^e$mainly III$^3$V$^3$Fuc$_2$nLc$_6$ staining
The procedures used are as described under "Experimental Procedures" using antibodies shown in Table 4.

TABLE 4

| | Antibodies Used in This Study | | |
|---|---|---|---|
| Antibody | Specificity | ATCC Number | Reference |
| 2D4 | asialo GM$_2$ | TIB 185 | 51 |
| 38.13 | Gb$_3$ structure | | 52 |
| J1 | Lc$_3$ structure | | 50 |
| 1B2 | type 2 chain lacto series | TIB 189 | 53 |
| BE2 | H antigens on type 2 chains | TIB 182 | 53 |
| H1B4 | H antigens on types 1 & 2 chains | | |
| Lewis a | Le$^a$ structure | CRL 1670 | 54 |
| Lewis b | Le$^b$ structure | HB 8326 | 55 |
| 1116-NS-19-9 | sialyl Le$^a$ | HB 8059 | 11 |
| WGHS-29-1 | Le$^x$ structure | | 14 |
| AH6 | Le$^y$ structure | | 18 |
| FH6 | sialyl Le$^x$ | | 16 |

11. Koprowski, et al, *Somatic Cell Genet.*, 5, 957–972 (1979).

These results indicate that similar glycolipid profiles and lack of significant quantities of lacto-series antigens are shared with both normal colonic mucosa and the colonic epithelial cell line. In addition, both adenocarcinoma tumors and cell lines have accumulations of a diversity of both type 1 and 2 chain based carbohydrate antigens.

EXAMPLE 6

Pathway of synthesis of type 1 and 2 chain based glycolipid antigens in normal colonic epithelial and colonic adenocarcinoma cell lines In order to isolate the specific enzymatic lesion associated with the expression of lacto-series antigens in adenocarcinomas but not in normal colonic epithelial cells, the activities of several enzymes involved in the synthesis of these antigens were determined and compared between normal epithelial and adenocarcinoma cells.

The pathway of synthesis and specific activity of the enzyme catalyzing each step in normal colonic epithelial and colonic adenocarcinoma cell lines is shown in Table 6. For the purposes of comparison between cell lines, results are reported as specific activities in crude cell homogenates.

TABLE 6

Pathway of Synthesis of Lacto-Series Antigens and Specific Activity of Associated Glycosyltransferases in Crude Homogenates of Normal Colonic Mucosal and

TABLE 6-continued
Colonic Adenocarcinoma Cell Lines

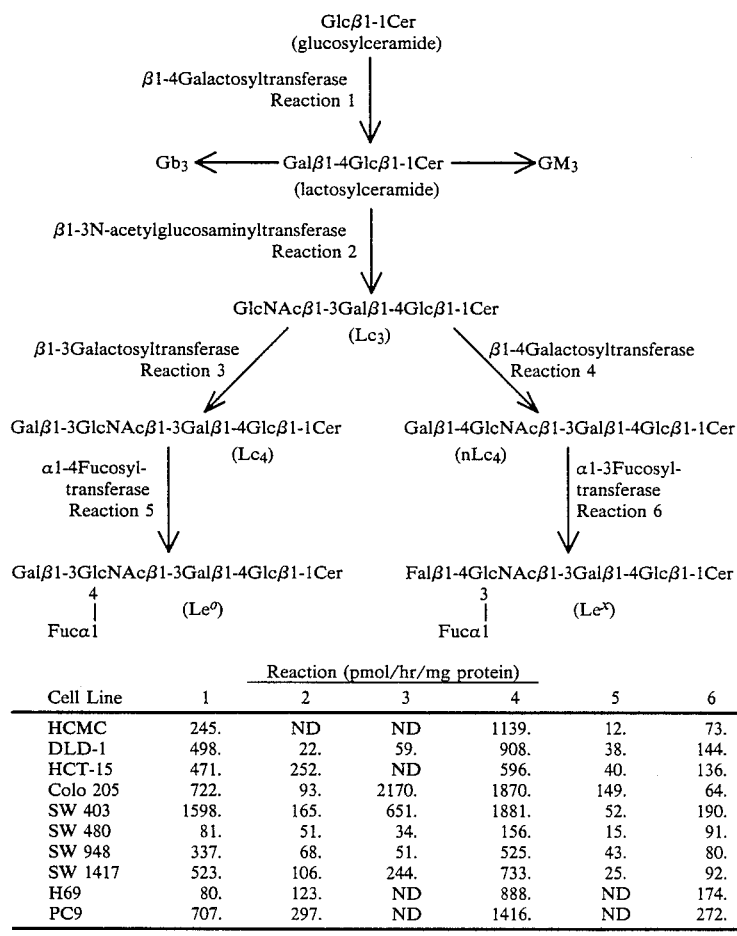

| Cell Line | Reaction (pmol/hr/mg protein) | | | | | |
|---|---|---|---|---|---|---|
| | 1 | 2 | 3 | 4 | 5 | 6 |
| HCMC | 245. | ND | ND | 1139. | 12. | 73. |
| DLD-1 | 498. | 22. | 59. | 908. | 38. | 144. |
| HCT-15 | 471. | 252. | ND | 596. | 40. | 136. |
| Colo 205 | 722. | 93. | 2170. | 1870. | 149. | 64. |
| SW 403 | 1598. | 165. | 651. | 1881. | 52. | 190. |
| SW 480 | 81. | 51. | 34. | 156. | 15. | 91. |
| SW 948 | 337. | 68. | 51. | 525. | 43. | 80. |
| SW 1417 | 523. | 106. | 244. | 733. | 25. | 92. |
| H69 | 80. | 123. | ND | 888. | ND | 174. |
| PC9 | 707. | 297. | ND | 1416. | ND | 272. |

The reaction mixtures were as described under "Experimental Procedures"
ND = none detected The initial reaction involves synthesis of lactosylceramide from the precursor glucosylceramide catalyzed by $\beta$1-4galactosyltransferase. This activity is variable but is highly expressed in normal mucosal cells and in all adenocarcinoma cell lines tested. Lactosylceramide is a common precursor for a variety of competing glycosyltransferases as shown. One fate of lactosylceramide is lacto-series chain synthesis catalyzed by $\beta$1-3N-acetylglucosaminyltransferase to form the product Lc$_3$ (reaction 2). This activity was also variable but found in all transformed cell lines tested, however no activity was detected in the normal epithelial HCMC cells. No detectable hydrolysis of [$^{14}$C]-GlcNAc labelled Lc$_3$ by endogenous $\beta$-N-acetylglucosaminidase was found for any of the cell lines tested over a 2 hour incubation period indicating that the observed differences in $\beta$1-3N-acetylglucosaminyltransferase activity reflects altered biosynthesis rather than degradation (results not shown).

Synthesis of type 1 and 2 chain structures Lc$_4$ and nLc$_4$ are catalyzed by $\beta$1-3 and $\beta$1-4galactosyltransferases, respectively, competing for Lc$_3$. A $\beta$1-4- galactosyltransferase responsible for transfer of Gal to Lc$_3$ in human plasma was previously reported to be lactose synthetase A protein which was also involved in the synthesis of lactosylceramide (J. Biochem., 92, 1123-1127 (1982)). This was confirmed in adenocarcinoma cells as shown in FIG. 8. The effect of increasing $\alpha$-lactalbumin on the $\beta$1-4galactosyltransferase activity in SW403 cells is seen with glucosylceramide and Lc$_3$ as acceptors. A similar decrease in transfer to each acceptor with increasing $\alpha$-lactalbumin concentration was observed indicating that this membrane bound enzyme is similar to lactose synthetase A protein. Slight activation of $\beta$1-3galactosyltransferase with Lc$_3$ as acceptor was found due presumably to the reduced substrate competition with the inhibited $\beta$1-4galactosyltransferase.

Formation of fucosylated derivatives of type 1 and 2 chains generated in the previous reactions are catalyzed by either $\alpha$1-3 or $\alpha$1-4fucosyltransferase activities. Significant but variable amounts of both activities were found in normal mucosal and adenocarcinoma cell lines. In contrast, the lung carcinoma cell lines tested contained only $\alpha$1-3 specific fucosyltransferase. Multiple fucosyltransferases have been described in human tissues, i.e. both $\alpha$1-3 specific (J. Biol. Chem., 260. 7619-7627 (1985), Eur. J. Biochem., 30, 269-277 (1972), Eur. J. Biochem., 130, 347-351 (1983)) and $\alpha$1-$\frac{3}{4}$ specific (J. Biol. Chem., 256, 10456-10463 (1981), Biochem. Biophys. Res. Commun., 100, 1611-1618 (1981), FEBS Lett., 142, 77-80 (1982)) fucosyltransferases exist in humans, the latter being associated with Le-gene expression. The nature of these activities in colon derived cells was tested by kinetic studies to gain information whether a single or multiple enzymes are present which catalyze transfer of fucose in α1-3 and/or α1-4 linkages. These results are shown in Table 7.

TABLE 7

Substrate competition studies with fucosyltransferase from homogenates of normal colonic mucosa, colonic adenocarcinoma and small cell lung carcinoma cells.

| | pmol [$^{14}$C]fucose transferred/hr/mg protein to: | | | | |
|---|---|---|---|---|---|
| Enzyme Source | Lc$_4$ | nLc$_4$ | Lc$_4$ + nLc$_4$ | One enzyme | Two enzymes |
| HCMC | 11. | 74. | 48. | 40. | 85. |
| DLD-1 | 38. | 144. | 115. | 87. | 182. |
| HCT-15 | 40. | 136. | 93. | 84. | 176. |
| SW 480 | 15. | 91. | 77. | 50. | 106. |
| SW 948 | 43. | 80. | 82. | 56. | 123. |
| SW 1417 | 25. | 92. | 73. | 56. | 117. |
| NCI-H69 | ND | 174. | 163. | | |

Reaction mixtures were as described under "Experimental Procedures" and contained 40 μg of Lc$_4$, nLc$_4$, or 40 μg of both Lc$_4$ and nLc$_4$. Calculated values for activity with mixed acceptor composition were determined using the following equations.

Two enzymes $v_t = v_a + v_b$

One enzyme $v_t = \dfrac{V_a a/K_a + V_b b/K_b}{1 + a/K_a + b/K_b}$

ND = none detected

ND=none detected.
Assays containing both Lc$_4$ and nLc$_4$ yielded total transfer of $^{14}$C-fucose in excess of that predicted if a single enzyme were present. This is most probably due to the presence of some H-gene and/or Se-gene α1-2-fucosyltransferase in these cells, the products of which are not resolved on TLC from α1-3 and α1-4 fucosyl products. Transfer of fucose to Lc$_4$ and nLc$_4$ when mixed with a non-fucosyl acceptor such as Gb$_4$ yielded the same activity as when they were assayed alone indicating that mixing acceptors does not in itself lower the resulting activity (results not show:). These results suggest that although formation of α1-2 fucosyl products may occur, and since the activity with mixed acceptors is far from additive compared to the acceptors by themselves, the most probable conclusion is the presence of an enzyme capable of transferring fucose in either α1-3 or α1-4 linkages in colonic mucosal and adenocarcinoma cells. Thus, the finding of type 2 chain fucosylated antigens in human colonic adenocarcinoma cells and tumors is most probably also associated with Le-gene expression as has been previously reported for expression of Lewis antigens (*Lancet*, 1332-1333 (1982)).

The products formed by transfer of fucose to different type 2 chain acceptors catalyzed by the α1-¾ specific enzyme from normal mucosal and adenocarcinoma cells were compared to those catalyzed by the α1-3 specific enzyme from NCI-H69 cells and is shown in FIG. 9. For each enzyme from either normal or transformed cells the same pattern of reaction products was observed In particular, the α1-¾ specific enzyme from normal colonic mucosal HCMC cells and from the colonic adenocarcinoma cell line yielded a single Le$^x$ reactive band from nLc$_4$ and two products that were Le$^x$ reactive from transfer to nLc$_6$ which co-migrated with V$^3$FucnLc$_6$ and III$^3$V$^3$Fuc$_2$nLc$_6$. Synthesis of polyfucosyl structures is in common with results shown here and previously reported for the α1-3 specific enzyme (*J. Biol. Chem.*, 260, 7619-7627 (1985)) and with results from structural studies with colonic adenocarcinoma tumors (*J. Biol. Chem.*, 259, 4672-4680 (1984)).

These results indicate that cell lines from normal colonic epithelium and adenocarcinomas behaved very similarly as normal mucosa and adenocarcinoma tumors in terms of expression of glycolipid antigens and enzymes involved in the synthesis. The most significant finding is that expression of both type 1 and 2 chain based lacto-series antigens is correlated with the expression in adenocarcinomas of a β1-3N-acetylglucosaminyltransferase which is not found in normal colonic epithelial cells. The alteration in the activity of this enzyme is the specific enzymatic lesion associated with the production of the entire series of both type 1 and 2 chain based lacto-series antigens in adenocarcinomas.

EXAMPLE 7 in situ biosynthesis of type 2 chain structures in epithelial cells of normal human colonic mucosa In order to confirm the above conclusion that alteration of a β1-3N-acetylglucosaminyltransferase is the enzymatic lesion responsible for the occurrence of lacto-series based antigens in adenocarcinomas, the following experiment was performed. Freshly obtained normal adult colonic tissue was obtained and cryostat sectioned. A solution containing the product of the proposed missing enzyme, Lc$_3$, was layered over the tissue sections. Glycolipids under this condition will be absorbed by the cell membranes of the tissue. Once the Lc$_3$ is absorbed by the membranes, a reaction mixture containing UDPGal is incubated with the sections, and the presence of the type 2 chain product nLc$_4$ is detected by a monoclonal antibody (1B2) specific for type 2 chain core structures. The ability of normal colonic epithelial cells to catalyze the synthesis of nLc$_4$ would support the notion that synthesis of its immediate precursor is limiting in normal colon epithelial cells.

Demonstration of in situ biosynthesized nLc$_4$ from added Lc$_3$ in normal adult proximal colon epithelial cells using the procedures described in Methods is shown in FIG. 10. This figure indicates that sections of normal colonic mucosa contain almost no detectable N-acetyllactosaminyl residues based on antibody 1B2 binding after pre-incubation of the sections with Lc$_3$ in PBS (Panel A). Incubation of sections in the absence of Lc$_3$ pre-incubation with a reaction mixture containing UDPGal had no effect on the nature of antibody binding (Panel B). However, pre-incubation of the sections with Lc$_3$ in PBS for 4 hours prior to incubation with UDPGal containing reaction mixtures yielded a product which was detected by binding of antibody 1B2 (Panel C). The adsorption of Lc$_3$ by the membranes and subsequent transfer of β1-4 linked galactose was highest and easily detectable in the epithelial cells of the normal mucosa. Panel D shows binding of antibody 1B2 to sections which were pre-incubated in the presence of nLc$_4$. A more generalized staining by the antibody is observed. Pre-incubation of tissue sections with irrelevant glycolipids yielded no antibody binding (results not shown). These results indicate that Lc$_3$ exogenously added to normal mucosa tissue sections can be incorporated into the membranes of colonic epithelial cells and in the presence of UDPGal, an epithelial cell derived β1-4galactosyltransferase catalyzes the formation of nLc$_4$. These results further indicate that the enzymatic activity responsible for appearance of lacto-series antigens during development and in association with oncogenesis in a β1-3N-acetylglucosaminyltransferase which is responsible for synthesis of Lc₃.

EXAMPLE 8

Pattern of expression of glycosyltransferase activities in normal colonic mucosa and colonic adenocarcinoma tumors The specific activities of glycosyltransferases associated with synthesis of lacto-series glycolipids is compared as crude tissue homogenates from several samples of scraped normal colonic mucosa and colonic adenocarcinoma tumors as shown in Table 8.

TABLE 8

Specific Activity of Glycosyltransferase Activities Associated with Synthesis of Type 2 Lacto-Series Antigens in Crude Homogenates of Normal Human Colonic Mucosa and Colonic Adenocarcinoma Tumors.

| Enzyme Source | β1→3GlcNAc transferase pmol/hr/ mg protein | β1→4Gal transferase pmol/hr/ mg protein | α1→3Fuc transferase pmol/hr/ mg protein |
|---|---|---|---|
| Normal mucosa case #1 | 18. ± 2 | 459. ± 8 | 167. ± 11 |
| Normal mucosa case #2 | 25. ± 2 | 772. ± 17 | 299. ± 14 |
| Normal mucosa case #3 | 18. ± 3 | 445. ± 9 | 199. ± 12 |
| Adenocarcinoma case 277-1 | 133. ± 5 | 853. ± 19 | 146. ± 9 |
| Adenocarcinoma case 297-1 | 276. ± 7 | 1290. ± 22 | 140. ± 6 |
| Adenocarcinoma case 464-1 | 100. ± 4 | 677. ± 8 | 80. ± 3 |

The reaction mixtures were as described under "Experimental Procedures". The variation between duplicate determinations in shown.

The specific activity of β1-3N-acetylglucosaminyltransferase is increased 6-to 11-fold in homogenates of colonic adenocarcinoma tumors compared to scraped normal adult colonic mucosa. The activities of β1-4-galactosyltransferase and α1-3fucosyltransferase associated with synthesis of Le$^x$ determinant structures from the immediate precursor Lc₃ were found in all tissue samples although the fucosyltransferase was generally lower in the tumors. The reason for this is unclear and may relate to decreased relative stability of the fucosyltransferase compared to the other enzymes in the tumors as glycolipids extracted from these tumors contained abundant accumulations of fucosylated glycolipids characteristic of colonic adenocarcinomas (results not shown). The scraped mucosa used in these experiments is not a uniform population of epithelial cells but contains in addition cells of connective tissue and infiltrative cells such as leukocytes. Results shown in Examples 1 to 4 indicated that type 2 lacto-series core chains containing β1-3 linked GlcNAc residues are not expressed in the epithelial cells of normal adult mucosa. This low β1-3N-acetylglucosaminyltransferase activity detected in scraped normal mucosa is most probably from non-epithelial cells.

These results indicate that significant increases in β1-3N-acetylglucosaminyltransferase are characteristic of colonic adenocarcinomas relative to normal mucosa indicating further the critical nature of the enhancement of this activity during oncogenesis in this tissue. In addition, these clear differences indicate potential for monitoring of this activity or action of the enzyme for diagnostic or prognostic purposes.

DISCUSSION

The results described in Examples 1 to 4 indicated that control of expression of type 2 chain based tumor-associated antigens in normal mucosal epithelial cells and adenocarcinoma tumors was mediated through expression of core chain synthesis in epithelial cells. The results from Examples 5 to 8 extend this to indicate that activation of a β1-3N-acetylglucosaminyltransferase is the enzymatic lesion responsible for formation of all lacto-series tumor-associated antigens found in adenocarcinomas. This enzyme is not detectable in normal colonic epithelial cells. Furthermore, when normal colon tissue is supplemented with the reaction product, type 2 chain structures are synthesized. The data presented also indicates that all of the adenocarcinoma cell lines tested expressed this activity and that its expression correlated with the finding of a wide diversity of carbohydrate structures based on both type 1 and 2 lacto-series core chains. A variety of other enzymes associated with tumor marker synthesis were analyzed. These included β1-4galactosyltrasferase which is involved in the synthesis of lactosylceramide or nLc₄, β1-3galactosyltransferase involved in the synthesis of Lc₄, and α1-¾fucosyltransferase which catalyzes the synthesis of Le$^a$ and Le$^x$ antigens. In each case, none of these activities correlated with the finding of lacto-series antigens in tumor cells and tissues but were absent in normal epithelial cells. Reports in the literature indicate an extremely wide variety of glycolipid structures based on either type 1 or 2 lacto-series chains have been found in adenocarcinomas and defined as tumor associated. A variety of competing transferases can yield a diversity of end-stage products. Depending upon the specific nature of other activities capable of modifying lacto-series chain structures in specific cell populations of colon tumors, many extended derivatives such as Le$^x$ and polyfucosyl Le$^x$ (Biochem. Biophys. Res. Commun., 109, 36–44 (1982), J. Biol. Chem., 259, 4672–4680 (1984)), sialyl Le$^x$ (J. Biol. Chem., 259. 10511–10517 (1984)), Le$^y$ (J. Biol. Chem., 258, 11793–11797 (1983)), or trifucosyl Le$^y$ (J. Biol. Chem., 261, 11247–11253 (1986)) have been found. Thus, although a variety of derivatives are present, the same enzymatic alteration is responsible for their expression and so, they are essentially equivalent with respect to their potential for markers of this process. The presence of large quantities of these antigens in colon tumors tend to obscure the nature of the specific enzyme alteration which leads to their synthesis.

Activation of a β1-3N-acetylglucosaminyltransferase in association with oncogenesis has been shown to be responsible for tumor marker expression. As a result expression of both type 1 and 2 chain based antigens is controlled by the same enzymatic lesion. An apparent paradox is the previous finding of type 1 chain based Le$^a$ antigens in normal mucosal epithelial cells and tissues. This appears to be due to the greater avidity of antibodies specific for type 1 chain structures compared to those specific for type 2 chain structures. Thus, a very low activity of the β1-3N-acetylglucosaminyltransferase which is undetectable in enzyme assays is most probably found in colonic epithelial cells which is responsible for the formation of only immunologically detectable quantities of these structures. In any case, as a consequence of activation of this enzyme, both type 1 and 2 chain based antigens are formed in association with oncogenesis. Therefore, alteration in expression of this activity should have a more comprehensive marker for this process and have greater diagnostic or prognostic potential.

THIRD SERIES OF EXAMPLES

The nature of the β1-3N-acetylglucosaminyltransferase induced in colonic adenocarcinoma cell lines and absent in normal colonic epithelial cells was characterized in terms of its properties and discussed in this third series of Examples.

EXAMPLE 9

Solubilization of β1-3N-acetylglucosaminyltransferase from SW403 cells

To study the β1-3N-acetylglucosaminyltransferase associated with tumor marker synthesis the enzyme was solubilized from tumor cells and characterized. The β1-3N-acetylglucosaminyltransferase activity to lactosylceramide was solubilized from a 27,000 x g membrane pellet of SW403 cells by 0.2% Triton X-100. The majority of the activity was obtained in the 100,000 × g supernatant fraction. The recovery of the β1-3N-acetylglucosaminyltransferase activity in this fraction was 74% compared to the crude homogenate.

Characterization of the β1-3N-acetylglucosaminyltransferase Effect of detergent and pH on activity The effect of various detergents on transfer of GlcNAc to lactosylceramide catalyzed by the solubilized enzyme from SW403 cells was tested and shown in Table 9. The results indicate that a variety of detergents whether non-ionic or ionic stimulate the reaction. The condition which yields the highest activity involves assay in the presence of added Triton CF-54 at a final concentration of 0.3%. The result reported for no additional detergents reflects the effect of a final concentration of Triton X-100 of 0.05% which was added along with the solubilized enzyme.

TABLE 9

| Effect of detergents on β1→3N-acetylglucosaminyltransferase activity | |
|---|---|
| Detergent | pmol/hr/mg protein |
| None[a] | 15. ± 2 |
| Brij 58 | 10. ± 2 |
| Triton X-100 | 68. ± 4 |
| Triton CF-54 | 80. ± 3 |
| Deoxycholate | 68. ± 4 |
| Taurodeoxycholate | 26. ± 3 |
| G-3634-A | 51. ± 4 |
| CHAPSO | 55. ± 3 |

The reaction mixtures were as described under "Experimental Procedures". Detergents were added at a final concentration of 0.3% The variation between duplicated determinations in shown.

[a]A final concentration of Triton X-100 of 0.05% was added to each reaction mixture along with the detergent solubilized enzyme.

The pH dependence of the enzyme was studied with a variety of buffers present at 50 mM final concentration at pH values varying from 4.5 to 8.5. These results are shown in FIG. 11. The enzyme was most active over a broad pH range from 5.8 to 7.5. The highest activity, however, was obtained with HEPES buffer at pH values from 7.0 to 7.2.

Requirements of β1-3N-acetylglucosaminyltransferase for optimal activity

Transfer of GlcNAc to lactosylceramide was tested under a variety of conditions as shown in Table 10. The complete system was composed of 10 mM $Mn^{++}$, 0.3% Triton CF-54, 5 mM CDPcholine, 40μg lactosylceramide, and 1 mM UDP[$^{14}$C]GlcNAc. The dependence on $Mn^{++}$ was quite strict as substitution with $Mg^{++}$ and $Ca^{++}$ yielded 21- and 13-fold less activity, respectively, when present at a final concentration of 10 mM. The metal ion requirement is absolute as substitution of $Mn^{++}$ with EDTA at 10 mM final concentration abolished all activity. Removal of Triton CF-54 or the exogenous acceptor lactosylceramide greatly diminished the activity. Assays involving relatively crude enzyme preparations routinely contain hydrolytic activities which can either destroy the sugar nucleotide donor or the labeled product. Removal of CDPcholine from the reaction mixture caused a significant loss of activity, whereas inclusion of a β-N-acetylhexosaminidase inhibitor GlcNAc caused only slight stimulation of the activity.

TABLE 10

| β1→3N-acetylglucosaminyltransferase reaction requirements | |
|---|---|
| Condition | pmol/hr/mg protein |
| complete | 76. ± 4 |
| $-Mn^{++}$, plus $Mg^{++}$ | 4. ± 1 |
| $-Mn^{++}$, plus $Ca^{++}$ | 6. ± 1 |
| $-Mn^{++}$, plus $Cu^{++}$ | 10. ± 2 |
| $-Mn^{++}$, plus $Co^{++}$ | 13. ± 2 |
| $-Mn^{++}$, plus $Cd^{++}$ | 13. ± 1 |
| $-Mn^{++}$, plus $Zn^{++}$ | 7. ± 1 |
| $-Mn^{++}$, plus $Ni^{++}$ | 8. ± 1 |
| $-Mn^{++}$, plus EDTA | ND |
| -Triton CF-54 | 12. ± 2 |
| -lactosylceramide | 8. ± 1 |
| -CDPcholine | 65. ± 3 |
| +GlcNAc | 80. ± 4 |

The reaction mixture were as described under "Experimental Procedures", Divalent metal ions were present at a final concentration of 10 nM. GlcNAc was added at a final concentration of 10 nM where indicated. The variation between duplicate determinations is shown.

ND=none detected

Kinetics of β1-3N-acetylglucosaminyltransferase activity.

Figure 12A:
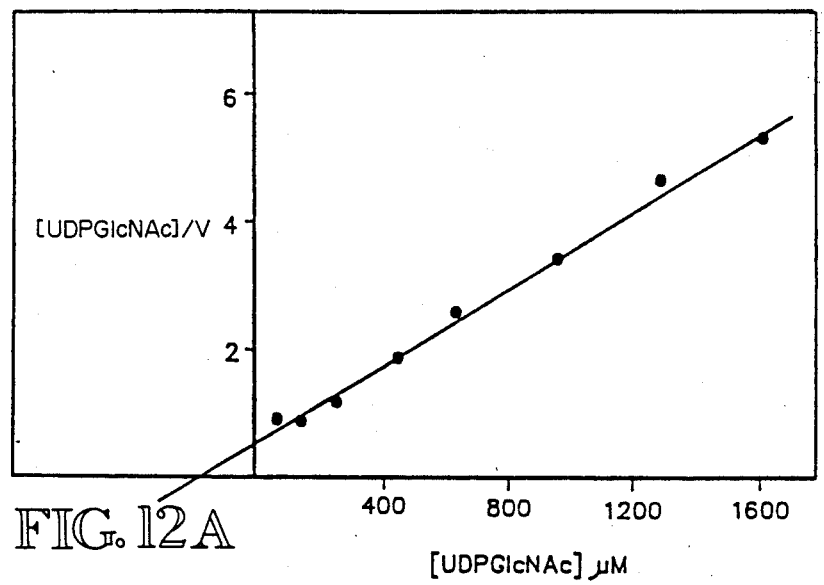
FIG. 12 shows the kinetic parameters from a Hanes-Woolf plot of saturation data with β1–3N-acetylglucosaminyltransferase.

Experiments to define the kinetic constants for various GlcNAc acceptors were conducted. These results are shown in FIG. 12A. A Hanes-Woolf plot of saturation data for acceptors $nLc_4$ and $nLc_6$ indicates essentially equivalent $K_m$ values of 0.19 mM for each. Saturation data for lactosylceramide could not be obtained due to the significant contribution from endogenous acceptor. The $V_{max}$ values determined for $nLc_4$ and $nLc_6$ were 150 and 110 pmol/hr/mg protein, respectively.

Figure 12B:
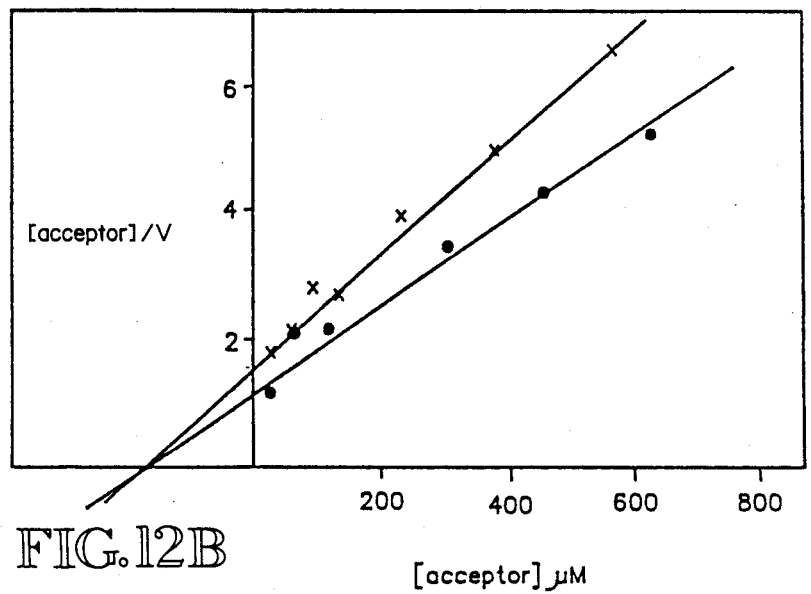

Saturation of the enzyme with UDPGlcNAc with lactosylceramide as the acceptor was also tested as shown in FIG. 12B. The results from a HanesWoolf plot of the saturation data indicated a rather high Km value of 0.17 mM.

Linearity of the reaction with time and protein concentration

The effect of increasing time and protein on the transfer of GlcNAc to lactosylceramide under the optimal conditions defined above is shown in FIG. 13. Transfer of GlcNAc is proportionate to time of incubation for at least 3 hours (Panel A), and proportionate to the amount of solubilized protein added from 100 to 500 μg per reaction mixture (Panel B).

Acceptor specificity of SW403 cell β1-3N-acetylglucosaminyltransferase

The quantitative results from transfer of GlcNAc to several lacto-series glycolipid acceptors is shown in Table 11. The results indicate that transfer to underivatized type 2 lacto-series chains is highest with this enzyme. Transfer to the type 1 chain structure Lc$_4$ is also detectable but is much lower. The enzyme transfers only to underivatized structures as no detectable transfer to any fucosylated derivative of either type 1 or 2 chains was observed.

TABLE 11

| Substrate specificity of β1→3N-acetylglucosaminyltransferase | |
|---|---|
| Acceptor | pmol/hr/mg protein |
| lactosylceramide | 76. ± 4 |
| nLc$_4$ | 160. ± 6 |
| Lc$_4$ | 27. ± 2 |
| nLc$_6$ | 99. ± 4 |
| III$^3$FucnLc$_4$ | ND |
| V$^3$FucnLc$_6$ | ND |
| III$^3$V$^3$Fuc$_2$nLc$_6$ | ND |
| III$^4$FucLc$_4$ | ND |

The reaction mixtures were as described under "Experimental Procedures". The assays were conducted in the presence of 40 g of each acceptor. The variation between duplicate determinations is shown. ND=none detected

TLC analysis of reaction products from β1-3N-acetylglucosaminyltransferase.

FIG. 14 shows the TLC profile of the reaction products from incorporation of [$^{14}$C]GlcNAc into the acceptors described in Table 10. Strong bands are observed from transfer to lactosylceramide, nLc$_4$, and nLc$_6$ and migrate in a position consistent with the addition of a single sugar residue. As described above, formation of a band with Lc$_4$ as the acceptor was found (lane 7) but was much weaker than those with linkage by TLC immunostain analysis using the monoclonal antibody J1 which is specific for terminal β1-3 linked GlcNAc structures (Mol. Immunol., 21, 87-882 (1984)). For these assays, unlabelled GlcNAc was incorporated into lactosylceramide or endogenous acceptor glycolipids and the products subjected to immunostain analysis. Lanes 10-13 show these results and indicate the transfer of GlcNAc in β1-3 linkage to form Lc$_3$ from lactosylceramide. In addition, hydrolysis of terminally labelled GlcNAc residues from transfer to the acceptors shown in lanes 5-8 was tested. The results indicated that $^{14}$C-labelled GlcNAc was removed by treatment with jack bean β-N-acetylglucosaminidase (results not shown).

DISCUSSION

The results of characterization of this enzyme indicate that it behaves very similarly to the enzyme from serum. Major differences are with respect to the membrane bound nature of the tumor cell enzyme and a higher K$_m$ for UDPGlcNAc compared to the soluble enzyme from serum. Most probably the serum enzyme is a structurally similar enzyme as the membrane bound enzyme and may be released into serum by proteolytic activity.

EXPERIMENTAL PROCEDURES

MATERIALS

Normal human colonic mucosa was obtained from two individuals of blood group B and one of blood group 0. Human small cell lung carcinoma NCI-H69 cell line was obtained from the American Type Culture Collection (Rockville, Md.). GDP[$^{14}$C]fucose (28 mCi/mnol) and UDP[$^{14}$C]galactose (240 mCi/msol) were obtained from Amersham (Arlington Heights, Ill.). Unlabelled GDPfucose was prepared by the method of Ginsburg (Methods Enzymol., 8, 293–295 (1966)). Unlabelled UDPgalactose was obtained from Sigma (St. Louis, Mo.). Type 2 chain glycolipids nLc$_4$ and nLc$_6$ were prepared by desialylation of sialosyllactoneotetraosylceramide and sialosyllactonorhexaosylceramide, which were prepared from bovine erythrocytes (J. Biol. Chem., 253, 4031-4035 (1978)). Desialylation was performed in 1% acetic acid at 100° C. for 1 hour. Lc$_3$ was prepared from nLc$_4$ by overnight hydrolysis with jack bean β-galactosidase in 0.1 M citrate buffer, pH 4.5, containing 0.1% deoxycholate. Glycolipids with the Le$^x$ hapten structure, III$^3$FucnLc$_4$, V$^3$FucnLc$_6$, and III$^3$V$^3$Fuc$_2$nLc$_6$, were prepared from human colonic adenocarcinoma (J. Biol. Chem., 259, 4672-4680 (1984)). Lactotetraosylceramide (type 1 chain paragloboside) (J. Biol. Chem., 254, 9311-9316 (1979)) was isolated from human meconium. The monoclonal antibodies FH3, 1B2, BE2, and AH6 were obtained as previously described (J. Biol. Chem., 259. 4681-4685 (1984), J. Biol. Chem., 256,10967-10972 (1981), J. Biol. Chem., 258, 11793-11979 (1983)), and WGHS-29-1 (Arch. Biochem. Biophys., 217, 647-651 (1982)), which reacts with Le$^x$ determinants, was a gift from Dr. Hilary Koprowski, The Wistar Institute, Philadelphia, Pa. Anti-Le$^a$ antibodies were obtained from Chembiomed Ltd., Edmonton, Alberta. The cationic detergent G-3634-A was a gift from Dr. Subhash Basu, Notre Dame University, South Bend, Ind. All other reagents were of the highest purity commercially available.

METHODS

Cell culture

Cell lines PC9, NCI-H69, DLD-1, HCT-15, and Colo 205 were grown in RPMI 1640 medium supplemented with 10% fetal calf serum. The cell lines SW403, SW480, SW948, and SW1417 were grown in L-15 medium supplemented with 10% fetal calf serum. HCMC cells were grown in MEM medium containing nonessential amino acids in Earle's BSS, 20% fetal calf serum, and 10 μg/ml epidermal growth factor. These cells have been reported to be epithelial in origin, presumably from the lower two-thirds of the crypt (J. Natl. Cancer Inst., 69, 1271-1276 (1982)). The cells were harvested and passed every 7-10 days. The cells were scraped, centrifuged, and washed with phosphate-buffered saline (PBS), and stored frozen at −80° C.

Solubilization of glycosyltransferase activities from NCI-H69 cells

The following steps were performed at 0°–4° C. Cells, 6 ml, were thawed and homogenized in two volumes of 50 mM HEPES buffer, pH 7.2, 0.5 M sucrose, 1 mM EDTA by two strokes of a Potter-Elvehjem homogenizer. The crude homogenate was centrifuged at 27,000 xg for 30 minutes to separate membranes from soluble proteins. The resulting pellet fraction was then re-homogenized in the presence of two volumes of the above buffer containing Triton X.100 at 0.2% final concentration with two strokes of the homogenizer and centrifuged for 1 hour at 100,000 xg. The supernatant fraction was removed and the 0.2% Triton X-100 extraction step was repeated with an additional two volumes of the Triton X-100 containing buffer. The pooled supernatant fractions were then concentrated to the original volume of packed cells by ultrafiltration and centrifugation through a conical nitrocellulose membrane (Amicon Centraflo CF 25 membranes, Amicon Corp., Lexington, Mass. 02173). Except where indicated, the concentrated enzyme fraction was used for characterization of activities present in NCI-H69 cells. The enzyme could be stored frozen at −20° C. without considerable loss of activity.

Preparation of normal human colonic mucosa fraction

Samples of normal colon were obtained and stored frozen at −80° C. before use. The thawed tissue was washed extensively in PBS and the mucosal lining was scraped off by the sharp edge of a piece of objective glass, washed three times with PBS, and centrifuged at 2000 xg for 5 minutes at 4° C. A portion of each mucosal fraction was homogenized in two volumes of 50 mM HEPES buffer, pH 7.2, 0.5 M sucrose, 1 mM EDTA by two strokes of a Potter-Elvehjem homogenizer and used for characterization of enzyme activities present in normal colonic mucosa. Another portion of the mucosal fractions from the type "B" individuals was pooled and the glycolipids extracted as described below.

Extraction of glycolipids from tissues and cells

Glycolipids were isolated from 5 ml each of packed NCI-H69 cells and normal human colonic mucosal residue by extraction with 10 volumes of isopropanol/hexane/water (55:25:20) in a Waring blender followed by filtration in a Buchner funnel. The insoluble residue was re-extracted with 10 volumes of the same solvent followed by filtration. The combined filtrates were concentrated to near dryness and transferred to Spectrapor 3 membrane tubing (Spectrums Medical Industries, Los Angeles, Calif.) and dialyzed extensively against water. The solution was removed from the dialysis bag and concentrated to near dryness and dissolved in a solvent composed of $CHCl_3:CH_3OH:H_2O$ (30:60:8) and subjected to chromatography on DEAE-Sephadex A-25 according to the method of Yu and Ledeen (J. Lipid Res., 13, 680–686 (1972)) to separate neutral glycolipids from gangliosides. The neutral glycolipid fraction obtained from the passthrough of the DEAE-Sephadex column was concentrated to dryness and placed in a vacuum dessicator over $P_2O_5$ overnight followed by acetylation with 10 ml of pyridine and 5 ml of acetic anhydride. The acetylated glycolipid fraction was obtained by chromatography on a Fluorisil column (J. Lipid Res., 12, 257–259 (1971)). The deacetylated neutral glycolipid fractions and the dialyzed total ganglioside fractions obtained from DEAE-Sephadex chromatography were utilized in these studies.

Glycolipids from type 0 erythrocytes and tumor tissue were obtained as previously described (J. Biol. Chem., 259, 4672–4680 (1984)).

Enzyme assays

α1-3Fucosyltransferase

Unless otherwise specified, the α1-3fucosyltransferase activity was determined in reaction mixtures containing 2.5 μmol HEPES buffer, pH 7.2, 40 μg $nLc_4$, 100 μg G-3634-A, 1 μmol $MnCl_2$, 0.5 μmol CDPcholine, 15 μmol GDP[$^{14}$C]fucose (15,000 cpm μmol), and 15–150 μg protein in a total volume of 0.1 ml. The reaction mixture was incubated for 2 hours at 37° C. for 2 hours and terminated by the addition of 6 μmol of EDTA and 0.1 ml of $CHCl_3:CH_3OH$, 2:1. The entire reaction mixture was streaked onto a 4 cm wide strip of Whatman 3 paper and chromatographed with water overnight. The glycolipid remaining at the origin was extracted with 2–5 ml washes of $CHCl_3:CH_3OH:H_2O$, (10:5:1). The solvent was removed with a nitrogen stream and dissolved on 20 μl $CHCl_3:CH_3OH$ (2:1). An aliquot, 10 μl, was removed and spotted onto an HPTLC plate (Merck, Darmstadt, West Germany) and developed in a solvent of $CHCl_3:CH_3OH:H_2O$ (60:40:9) containing 0.02% $CaCl_2$ as a final concentration. Standard glycolipids were visualized by orcinol spray. Radioactive glycolipid bands were located by autoradiography, scraped from the plate, and counted by a liquid scintillation counter. One unit of activity is defined as transfer of one pico mol of fucose per hour under the conditions of the assay.

β1-3 and β1-4Galactosyltransferase

The reaction mixtures contained 2.5 μmol HEPES buffer, pH 7.0, 20 μg $Lc_3$, 10 μg deoxycholate, 1μmol $MnCl_2$, 0.5 μmol CDPcholine, 0.5 μmol galactonolactone, 15 μmol UDP[$^{14}$C]galactose (30,000 cpm μmol), and 0.1 mg protein in a total volume of 0.1 ml. The reaction was conducted for 1 hour at 37° C. and stopped by the addition of 6 μmol of EDTA and 100 μl of $CHCl_3:CH_3OH$ (2:1). The incorporation of [$^{14}$C]-galactose into glycolipid was determined as described above.

β1-3N-acetylglucosaminyltransferase

N-acetylglucosaminyltransferase assays were performed in reaction mixtures containing 2.5 μmol of HEPES buffer, pH7.2, 30 μg of lactosylceramide, 150 μg of Triton CF-54, 0.5 μmol of $MnCl_2$, 0.5 μmol of CDPcholine, 50 μmol of UDP[$^{14}$C]N-acetylglucosamine (5000 cpm μmol), and 200–400 μg of protein in a total volume of 0.05 ml. The reaction mixture was incubated for 2 hours at 37° C. and terminated by addition of 50 μl of 0.25M EDTA and 0.6 ml $CHCl_3:CH_3OH$ (2:1). The labelled product was extracted into the lower phase of a Folch extraction (J. Biol. Chem., 191, 819–831), dried by an $N_2$ stream, and dissolved in 20 μl of $CHCl_3:CH_3OH$ (2:1). An aliquot, 10 μl, was spotted on a HPTLC plate (Merck) and developed in a solvent composed of $CHCl_3:CH_3OH:H_2O$ (60:35:8). The labelled glycolipids were located by autoradiography, scraped, and quantitated in a liquid scintillation counter.

Protein determination

Protein concentrations were determined by the method of Lowry et al. (J. Biol. Chem., 193, 265–275 (1951)) using a bovine serum albumin standard.

Immunostaining of glycolipids

Immunostaining of glycolipids separated on HPTLC plates was performed using the procedure of Magnani et al. (*Anal. Biochem.*, 109, 399–402 (1980)) as modified by Kannagi et al. (*J. Biol. Chem.*, 257, 14865–14874 (1982)). Glycolipids were separated on an HPTLC plate (Si-HPTLC plate 7011-3, J.T. Baker Chemical Co., Phillipsburg, N.J.) using solvent systems composed of $CHCl_3:CH_3OH:H_2O$ (60:35:8), $CHCl_3:CH_3OH:H_2O$ (56:38:10), and $CHCl_3:CH_3OH:H_2O$ (60:40:9) containing 0.02% $CaCl_2H_2O$. After development, the plate was dried and soaked for 2 hours in 5% bovine serum albumin in PBS to block nonspecific antibody binding. The plate was then incubated in a 1:500 to 1:1000 diluted monoclonal antibody in PBS containing 1% bovine serum albumin overnight, followed by sequential incubations with 1:2000 diluted rabbit anti-murine Ig antibody solution and with [125I]-protein A solution. After extensive washes with PBS between each step and after [125I]-protein A treatment, the plate was dried and labelled bands were detected by autoradiography. Immunostain analysis of products from enzyme reactions were performed in the same way. The in vitro synthesized products were prepared using the assay conditions already described except that unlabeled sugar nucleotide donors were utilized. In each case control reaction mixtures without addition of exogenous glycolipid acceptor were run to monitor amounts of endogenous glycolipid staining.

Immunofluorescence studies of normal human fetal and adult colon tissue.

Fresh samples of normal adult proximal colon and fetal intestinal tissue were obtained and prepared for cryostat sectioning. The sections r were incubated with primary antibody specific for either $Le^x$, $Le^a$, or type 2 chain lacto-structures both before and after treatment of the tissue with *C. perfringes* neuraminidase. The sections were washed and treated with FITC-labelled secondary antibody. The washed sections were then examined by fluorescence microscopy.

In situ biosynthesis of $nLc_4$ in normal colon tissue sections

Surgical samples of normal colon from patients with non-malignant disease were obtained and immediately frozen for cryostat sectioning. Sections, 6 microns thick, were cut and washed in PBS. Glycolipids ($Lc_3$, $nLc_4$, or $Gg_4$) were adsorbed to the membranes of some of the sections by incubation in the presence of 0.1 mg glycolipid per ml of PBS for 4 hours at 4° C. At the end of this period, the sections were washed in PBS three times and finally in 50 mM HEPES buffer, pH7.0. An aliquot, 100 $\mu l$, of a reaction mixture containing 2.5 $\mu mol$ HEPES buffer, pH 7.0, 1 $\mu mol$ $MnCl_2$, 0.5 $\mu mol$ CDPcholine, 0.5 $\mu mol$ galactonolactone, with or without 50 $\mu mol$ UDPgalactose was layered over the appropriate tissue section and incubated for 3 hours at room temperature. The sections were then washed three times in PBS followed by incubation for 1 hour in PBS containing 5% goat serum. At the end of this period, 100 $\mu l$ of antibody 1B2 ascites diluted 1:100 in PBS containing 0.5% goat serum was layered over the tissue and incubated overnight at room temperature. After washing with PBS, the tissue was incubated with 1:40 diluted FITC-labelled rabbit anti-mouse whole Ig for 1 hour, washed extensively with PBS, and mounted for examination by fluorescence microscopy. Control tissue sections were run which contained either no or an irrelevant glycolipid ($Gg_4$) and also with and without UDPgalactose in the reaction mixture.

The embodiments of the invention in which an exclusive property or privilege is claimed are defined as follows:

1. A method for diagnostic or prognostic detection of a cancerous disease state in human secretory epithelia comprising analysis of $\beta$1-3N-acetylglucosaminyltransferase expression in a test specimen by enzyme activity wherein an increase of $\beta$1-3 N-acetylglucosaminyltransferase expression is observed in a cancerous disease state as compared with a healthy state.

2. The method of claim 1 wherein said cancerous disease state in secretory epithelia is colonic adenocarcinoma.

3. The method of claim 1 wherein said specimen is chosen from the group consisting of tissue and serum.

4. A method of detecting a cancerous disease state in secretory epithelia comprising:
   a. preparing a specimen from an individual,
   b. assaying enzyme activity of $\beta$1-3N-acetylglucosaminyltransferase in said specimen,
   determining the presence of a cancerous disease state by observing an increase in said enzyme activity in comparison with the enzyme activity observed in specimens from healthy individuals.

* * * * *